(12) United States Patent
Takada et al.

(10) Patent No.: US 9,929,355 B2
(45) Date of Patent: Mar. 27, 2018

(54) AMINE COMPOUND AND ORGANIC ELECTROLUMINESCENT DEVICE INCLUDING THE SAME

(71) Applicant: SAMSUNG DISPLAY CO., LTD., Yongin-si, Gyeonggi-do (JP)

(72) Inventors: Ichinori Takada, Yokohama (JP); Hiroaki Itoi, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 124 days.

(21) Appl. No.: 14/967,188

(22) Filed: Dec. 11, 2015

(65) Prior Publication Data
US 2016/0172593 A1 Jun. 16, 2016

(30) Foreign Application Priority Data

Dec. 15, 2014 (JP) .................................. 2014-252956

(51) Int. Cl.
*H01L 51/00* (2006.01)
*C07D 307/91* (2006.01)
(Continued)

(52) U.S. Cl.
CPC ........ *H01L 51/0074* (2013.01); *C07D 307/91* (2013.01); *C07D 333/76* (2013.01);
(Continued)

(58) Field of Classification Search
CPC ............. H01L 51/0051; H01L 51/0058; H01L 51/0061; H01L 51/0073; H01L 51/0074;
(Continued)

(56) References Cited

U.S. PATENT DOCUMENTS

2012/0056171 A1* 3/2012 Kim ........................ C09B 57/00
257/40
2013/0075715 A1 3/2013 Yokoyama et al.
(Continued)

FOREIGN PATENT DOCUMENTS

EP 2 468 725 A1 6/2012
JP 3079909 B2 8/2000
(Continued)

OTHER PUBLICATIONS

Abstract of Japanese Publication No. 7145372 A, Jun. 6, 1995 Corresponding to Japanese Patent No. 3079909 B2, Aug. 21, 2000, 1 Page.
(Continued)

*Primary Examiner* — Amanda C Walke
(74) *Attorney, Agent, or Firm* — Lewis Roca Rothgerber Christie LLP

(57) ABSTRACT

An amine compound is represented by the following Formula 1:

Formula 1

(Continued)

The amine compound may be included in at least one of the layers positioned between an anode and an emission layer of an organic electroluminescent device. The amine compound may improve the emission lifetime of the organic electroluminescent device including the amine compound.

18 Claims, 1 Drawing Sheet

(51) Int. Cl.
*C07D 333/76* (2006.01)
*H01L 51/50* (2006.01)

(52) U.S. Cl.
CPC ...... *H01L 51/0061* (2013.01); *H01L 51/0073* (2013.01); *H01L 51/0058* (2013.01); *H01L 51/5056* (2013.01)

(58) Field of Classification Search
CPC .. H01L 51/5056; C07D 307/91; C07D 333/76
USPC ............... 257/40; 428/690; 549/43, 460
See application file for complete search history.

(56) References Cited

U.S. PATENT DOCUMENTS

| | | | | |
|---|---|---|---|---|
| 2014/0191214 A1* | 7/2014 | Kim | ............ | H01L 51/006 257/40 |
| 2015/0065730 A1* | 3/2015 | Montenegro | ......... | C07C 211/54 548/440 |
| 2015/0243891 A1* | 8/2015 | Kato | ............ | C07D 333/76 257/40 |
| 2016/0028014 A1* | 1/2016 | Kim | ............ | H01L 51/0052 257/40 |
| 2016/0163993 A1* | 6/2016 | Nakano | .......... | C07C 211/58 257/40 |
| 2016/0197277 A1* | 7/2016 | Kato | ............ | H01L 51/006 257/40 |
| 2016/0260901 A1* | 9/2016 | Kim | ............ | H01L 51/006 |
| 2016/0372666 A1* | 12/2016 | Ryu | ............ | H01L 51/006 |

FOREIGN PATENT DOCUMENTS

| | | | |
|---|---|---|---|
| JP | 3983215 B2 | | 9/2007 |
| JP | 5739815 B2 | | 6/2015 |
| KR | 20150006199 A | * | 1/2015 |
| WO | WO 2011/059099 A1 | | 5/2011 |

OTHER PUBLICATIONS

Abstract of Japanese Publication No. 2005120030 A, May 1, 2005 Corresponding to Japanese Patent No. 3983215 B2, Sep. 26, 2007, 2 Page.

Abstract of European Publication No. 2502908 A1 Corresponding to Japanese Patent No. 5739815 B2, Jun. 24, 2015, 1 Page.

* cited by examiner

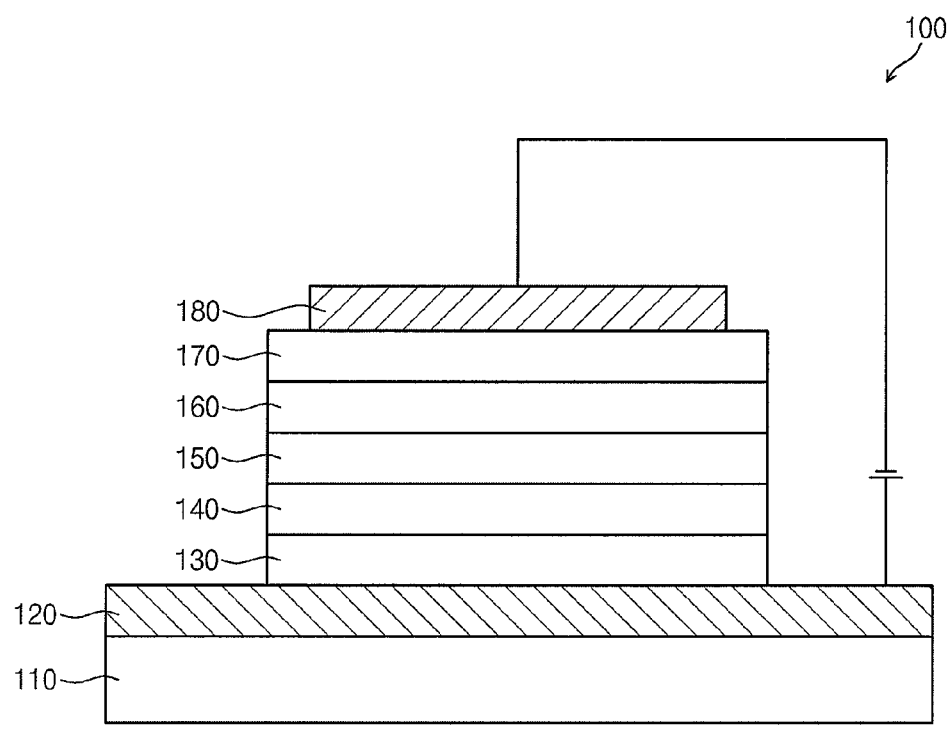

AMINE COMPOUND AND ORGANIC ELECTROLUMINESCENT DEVICE INCLUDING THE SAME

CROSS-REFERENCE TO RELATED APPLICATIONS

This U.S. non-provisional patent application claims priority under 35 U.S.C. § 119 of Japanese Patent Application No. 2014-252956, filed on Dec. 15, 2014, the entire content of which is hereby incorporated by reference.

BACKGROUND

1. Field

One or more aspects of embodiments of the present disclosure herein relate to an amine compound and an organic electroluminescent device including the same.

2. Description of the Related Art

Recently, organic electroluminescent displays have been actively developed. In addition, organic electroluminescent devices, which are self-emitting devices used in organic electroluminescent displays, have also been actively developed.

An example structure of an organic electroluminescent device includes an anode, a hole injection layer, a hole transport layer, an emission layer, an electron transport layer, an electron injection layer, and a cathode that are successively laminated (e.g., in the stated order). In such organic electroluminescent device, holes and electrons, respectively injected from the anode and the cathode, are recombined in the emission layer to generate excitons. Light is emitted when the generated excitons are transited (e.g., transition) to the ground state.

To improve the emission efficiency and emission lifetime of organic electroluminescent devices, various compounds have been investigated as material to be used in each lamination layer (e.g., in an anode, a hole injection layer, a hole transport layer, an emission layer, an electron transport layer, an electron injection layer, and/or a cathode). For example, an amine compound which can be used as a hole transport material in an organic electroluminescent device has been previously disclosed.

However, an organic electroluminescent device which uses the previously disclosed hole transport material has insufficient emission efficiency and/or device lifetime. Therefore, there is a demand for the development of a compound material which may improve the emission performance and/or device lifetime of an organic electroluminescent device.

SUMMARY

One or more aspects of embodiments of the present disclosure are directed toward a novel and enhanced amine compound which improves the emission efficiency and emission lifetime of an organic electroluminescent device, and an organic electroluminescent device including the amine compound.

An embodiment of the inventive concept provides an amine compound, represented by the following Formula 1:

Formula 1

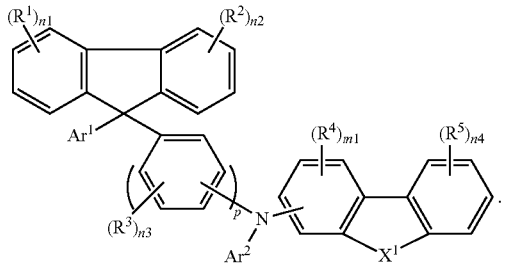

In the Formula 1, $X^1$ may be O or S; $Ar^1$ and $Ar^2$ may be each independently selected from a substituted or unsubstituted aryl group having 6 to 30 carbon atoms for forming a ring, and a substituted or unsubstituted heteroaryl group having 2 to 30 carbon atoms for forming a ring; $R^1$, $R^2$, $R^4$, and $R^5$ may be each independently selected from a substituted or unsubstituted alkyl group having 1 to 10 carbon atoms, a substituted or unsubstituted cycloalkyl group having 5 to 10 carbon atoms for forming a ring, a substituted or unsubstituted aryl group having 6 to 20 carbon atoms for forming a ring, and a 5- to 7-membered ring structure obtained through bonding of any adjacent substituents; $R^3$ may be a substituted or unsubstituted alkyl group having 1 to 10 carbon atoms; n1 to n4 may be each independently an integer selected from 0 to 4; m1 may be an integer selected from 0 to 3; and p may be an integer selected from 1 to 3.

The emission lifetime of an organic electroluminescent device may be improved using the amine compound of the embodiment.

In an embodiment, at least one of the p number of phenylene groups connecting a fluorenyl group and an arylamino group may connect the fluorenyl group and the arylamino group at a meta position.

The emission lifetime of an organic electroluminescent device may be improved using the amine compound of the embodiment.

In an embodiment, the $Ar^1$ may be a substituted or unsubstituted aryl group or a substituted or unsubstituted heteroaryl group, each independently obtained through 2- or 3-ring condensation of any of 5- to 6-membered aromatic and heteroaromatic rings.

The emission lifetime of an organic electroluminescent device may be further improved using an amine compound of the embodiment.

In an embodiment, the $Ar^2$ may be a substituted or unsubstituted aryl group or a substituted or unsubstituted heteroaryl group, each independently obtained through 2- or 3-ring condensation of any of 5- to 6-membered aromatic and heteroaromatic rings.

The emission lifetime of an organic electroluminescent device may be further improved using an amine compound of the embodiment.

In an embodiment, the $Ar^2$ may be represented by the following Formula 2:

Formula 2

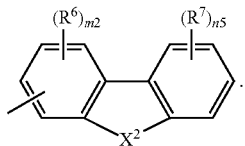

In the Formula 2, $X^2$ may be O or S; $R^6$ and $R^7$ may be each independently selected from a substituted or unsubstituted alkyl group having 1 to 10 carbon atoms, a substituted or unsubstituted cycloalkyl group having 5 to 10 carbon atoms for forming a ring, a substituted or unsubstituted aryl group having 6 to 20 carbon atoms for forming a ring, and a 5-7-membered ring structure obtained through bonding of any adjacent substituents; n5 may be an integer selected from 0 to 4; and m2 may be an integer selected from 0 to 3.

The emission lifetime of an organic electroluminescent device may be improved using an amine compound of the embodiment.

In another embodiment of the inventive concept, an organic electroluminescent device includes the amine compound in at least one of the plurality of lamination layers between an anode and an emission layer of an organic electroluminescent device.

The emission lifetime is improved in an organic electroluminescent device of the embodiment.

The amine compound may be included in a layer which is adjacent to the emission layer, and the emission lifetime may be improved in an organic electroluminescent device of the present embodiment.

BRIEF DESCRIPTION OF THE DRAWINGS

The accompanying drawing is included to provide a further understanding of the present inventive concept, and is incorporated in and constitutes a part of this specification. The drawing illustrates example embodiments of the inventive concept and, together with the description, serves to explain principles of the inventive concept. The drawing is a schematic diagram illustrating an organic electroluminescent device according to an embodiment of the present inventive concept.

DETAILED DESCRIPTION

Hereinafter, example embodiments of the present inventive concept will be described with reference to the accompanying drawing. Moreover, in the description and the drawing, like reference numerals refer to like elements or elements having like functions throughout, and repeated explanation thereof will not be provided herein.

Amine Compound According to an Embodiment of the Inventive Concept

First, description will be given of an amine compound according to an embodiment of the inventive concept. The amine compound according to an embodiment of the inventive concept is a compound which may be suited for use as a hole transport material in an organic electroluminescent device, and the amine compound may be represented by the following Formula 1:

Formula 1

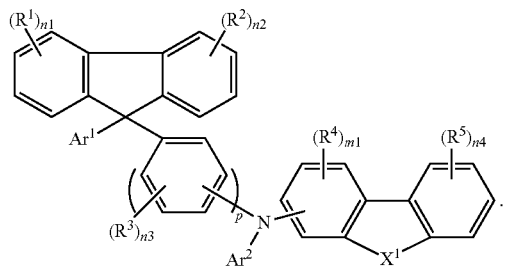

In the above Formula 1, $X^1$ may be O or S; $Ar^1$ and $Ar^2$ may be each independently selected from a substituted or unsubstituted aryl group having 6 to 30 carbon atoms for forming a ring, and a substituted or unsubstituted heteroaryl group having 2 to 30 carbon atoms for forming a ring; $R^1$, $R^2$, $R^4$, and $R^5$ may be each independently selected from a substituted or unsubstituted alkyl group having 1 to 10 carbon atoms, a substituted or unsubstituted cycloalkyl group having 5 to 10 carbon atoms for forming a ring, a substituted or unsubstituted aryl group having 6 to 20 carbon atoms for forming a ring, and a 5- to 7-membered ring structure obtained through ring condensation with any adjacent substituents, $R^3$ may be a substituted or unsubstituted alkyl group; n1 to n4 may be each independently an integer from 0 to 4; m1 may be an integer from 0 to 3; and p may be an integer from 1 to 3. As used herein, the expression "atoms for forming a ring" may refer to "ring-forming atoms."

In some embodiments, in the above Formula 1, $Ar^1$ may be unsubstituted by an amino group (e.g., may not be substituted by an amino group) and $Ar^2$ may exclude a fluorenyl group (e.g., may not include a fluorenyl group).

The amine compound represented by the above Formula 1 has a high hole mobility because an arylamino group having a high hole mobility is included in the molecular structure. In addition, the amine compound represented by Formula 1 also has a high resistance to electrons which have invaded from the emission layer (e.g., which may leak from the emission layer) because a dibenzoheterole ring (e.g., a moiety of Formula 1 in which two benzene rings are condensed to a 5-membered ring including $X^1$) having a high electron resistance is included in the molecular structure. Therefore, the emission lifetime of an organic electroluminescent device may be improved by using the amine compound of the present embodiments as represented by Formula 1 and having a high hole mobility and durability.

Moreover, steric hindrance in the vicinity of $Ar^1$ and $Ar^2$ in Formula 1 may be relieved because the amine moiety in the compound represented by the above Formula 1 is coupled to a fluorenyl group through at least one connecting group (e.g., at least one phenylene group). Therefore, in the amine compound represented by Formula 1, various molecular configurations of $Ar^1$ and $Ar^2$ become possible.

Furthermore, the amine compound represented by Formula 1 may be included in at least one layer which is disposed (e.g., positioned) between an anode and an emission layer of an organic electroluminescent device, so that the device lifetime (herein also referred to as "emission lifetime") of the organic electroluminescent device may be improved. For example, the amine compound represented by Formula 1 may be included in at least one of the layers selected from a hole injection layer and a hole transport layer.

For example, when the amine compound of an embodiment of the present disclosure represented by Formula 1 is included in a layer which is adjacent to the emission layer (for example, in a hole transport layer), an invasion and diffusion of electrons from the emission layer may be effectively prevented or reduced.

Moreover, in the above Formula 1, at least one of the p number of phenylene groups connecting a fluorenyl group and an arylamino group may connect the fluorenyl group and the arylamino group at a meta position. Herein, "connecting" may refer to connections between substituents through a connecting group (e.g., a phenylene group), as well as direct connections between substituents (e.g., via a bond such as a single bond). For example, in some embodiments, at least one of the p number of phenylene groups connecting a fluorenyl group and an arylamino group may be substituted at a meta position, where the substituents of each phenylene group are selected from a fluorenyl group, an arylamino group, and a phenylene group.

For example, when p=1, a fluorenyl group and an arylamino group may be connected at a meta position through a phenylene group in which a fluorenyl group and an arylamino group were substituted. For example, a fluorenyl group and an arylamino group may be directly connected to a phenylene group at a meta position. When p=2 or p=3, a fluorenyl group and an arylamino group may be connected at a meta position through a connecting group which includes at least one phenylene group and in which a fluorenyl group, an arylamino group, and/or a phenylene group were substituted. For example, a fluorenyl group and an arylamino group may be connected through a connecting group which includes 2 or 3 phenylene groups, each substituted with a phenylene group, a fluorenyl group, and/or an arylamino group, and at least one of these 2 or 3 phenylene groups may have the corresponding substituents coupled at a meta position.

When a fluorenyl group and an arylamino group are connected in the aforementioned configuration, the bulkiness of a side chain in the amine compound represented by Formula 1 may be increased. The bulkiness of the side chain may prevent or reduce the electrons from diffusing towards a hole transport layer. Therefore, the amine compound of an embodiment represented by Formula 1 may further improve the emission lifetime of an organic electroluminescent device.

In some embodiments, in the above Formula 1, $Ar^1$ may be a substituted or unsubstituted aryl or heteroaryl group obtained through 2- or 3-ring condensation of any of 5- to 6-membered aromatic and heteroaromatic rings. In some embodiments, $Ar^2$ may be a substituted or unsubstituted aryl or heteroaryl group obtained through 2- or 3-ring condensation of any of 5- to 6-membered aromatic and heteroaromatic rings.

A substituted or unsubstituted aryl or heteroaryl group obtained through 2- or 3-ring condensation of any of 5- to 6-membered aromatic and heteroaromatic rings may include, for example, a fluorenyl group, an anthryl group, a naphthyl group, a dibenzofuranyl group, a dibenzothiophenyl group, a carbazolyl group, a phenanthrenyl group, an indolyl group, a quinolyl group, etc., but is not limited thereto.

When $Ar^1$ and/or $Ar^2$ is a substituent as described above, the amine compound represented by Formula 1 may have a bulky molecular structure. Then the amine compound may have an improved electron blocking ability and may prevent or reduce the diffusion of electrons which are invading from the emission layer. Therefore, the amine compound of an embodiment represented by Formula 1 may further improve the emission lifetime of an organic electroluminescent device.

In some embodiments, in the above Formula 1, $Ar^2$ may be a substituent represented by the following Formula 2:

Formula 2

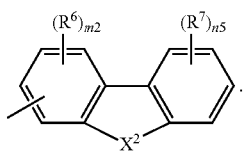

In the above Formula 2, $X^2$ may be O or S; $R^6$ and $R^7$ may be each independently selected from a substituted or unsubstituted alkyl group having 1 to 10 carbon atoms, a substituted or unsubstituted cycloalkyl group having 5 to 10 carbon atoms for forming a ring, a substituted or unsubstituted aryl group having 6 to 20 carbon atoms for forming a ring, and a 5- to 7-membered ring structure obtained through bonding of any adjacent substituents (e.g., through bonding of any adjacent $R^6$(s) or $R^7$(s)); n5 may be an integer from 0 to 4; and m2 may be an integer from 0 to 3.

When $Ar^2$ in Formula 1 is represented by Formula 2, the number of dibenzoheterole rings included in the molecular structure of the amine compound represented by Formula 1 and having a high resistance to electrons increases, and thus the resistance to electrons which are invading from the emission layer may be improved. Thus, an organic electroluminescent device which includes the amine compound of an embodiment represented by Formula 1 may have an improved emission lifetime.

As used herein, non-limiting examples of the aryl group and heteroaryl group may include a phenyl group, a biphenyl group, a terphenyl group, a naphthyl group, a phenylnaphthyl group, a naphthylphenyl group, an anthryl group, a phenanthrenyl group, a fluorenyl group, an indenyl group, a pyrenyl group, a fluoranthenyl group, a triphenylenyl group, a pyrazinyl group, a pyrrolyl group, a pyridyl group, a pyrimidyl group, a pyridazyl group, a pyrazinyl group, a furanyl group, a pyranyl group, a thienyl group, a quinolyl group, an isoquinolyl group, a benzofuranyl group, a dibenzothiophenyl group, an indolyl group, a benzoxazolyl group, a benzothiazolyl group, a quinoxalyl group, a benzoimidazolyl group, a pyrazolyl group, a tetrazolyl group, an imidazolyl group, an oxazolyl group, an isoxazolyl group, a thiazolyl group, an isothiazolyl group, a dibenzoheterolyl group, etc.

Non-limiting examples of the alkyl group may include a straight-chain (e.g., linear) alkyl group such as a methyl group, an ethyl group, a propyl group, a butyl group, an octyl group, a decyl group, etc., and a branched chain alkyl such as a t-butyl group, etc. Non-limiting examples of the cycloalkyl group may include a cyclopentyl group, a cyclohexyl group, a cycloheptyl group, a cyclooctyl group, etc.

Non-limiting examples of a substituent of the aryl and heteroaryl groups included in, for example, $Ar^1$ and $Ar^2$, may include any of the above-described alkyl, aryl, and heteroaryl groups, an alkoxy group, a trialkylsilyl group, an aryloxy group, an arylthio group, a triarylsilyl group, an alkyldiarylsilyl group, a dialkylarylsilyl group, etc. In some embodiments, the substituents of $Ar^1$ and $Ar^2$ may be further substituted by a like substituent, and adjacent substituents may bond with each other to form a 5- to 7-membered ring.

In some embodiments, an amine compound according to the present embodiments may be selected from Compounds 1 to 54 illustrated below and collectively denoted as Formulae 3 to 5. However, the amine compound according to the present embodiments is not limited to the following compounds.

Formula 3
1
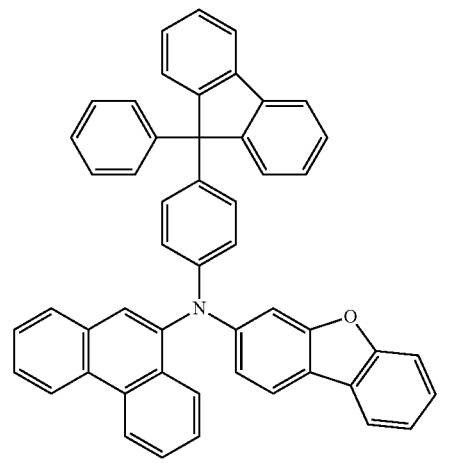
2
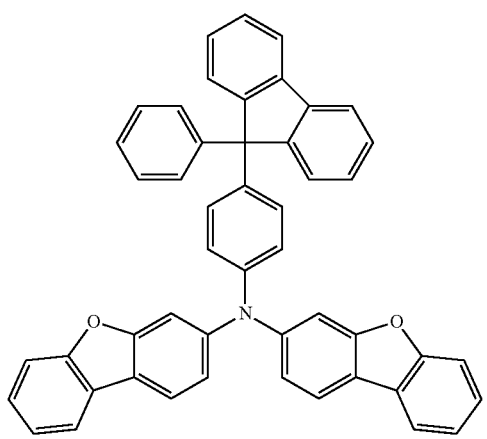
3
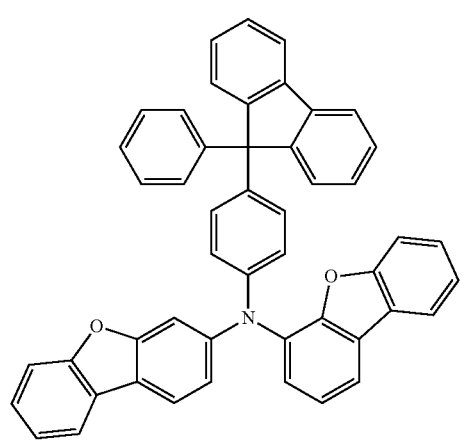
4
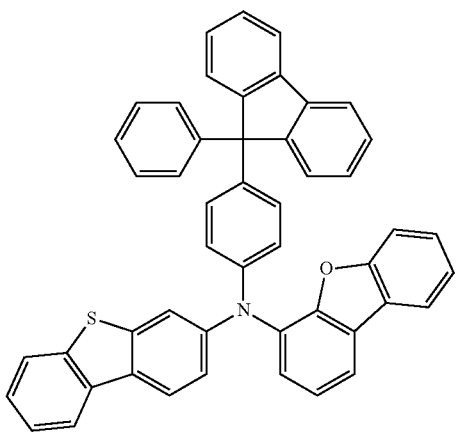
5
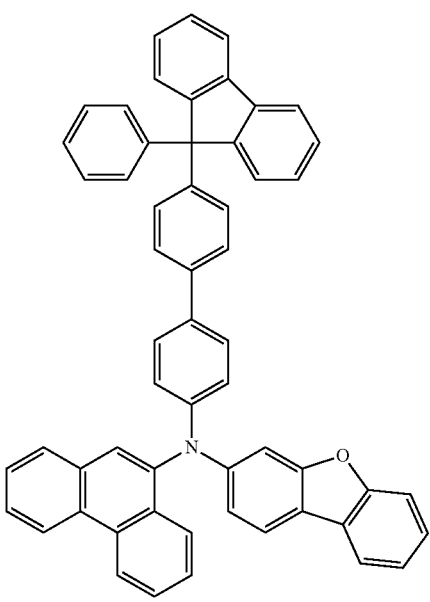
6
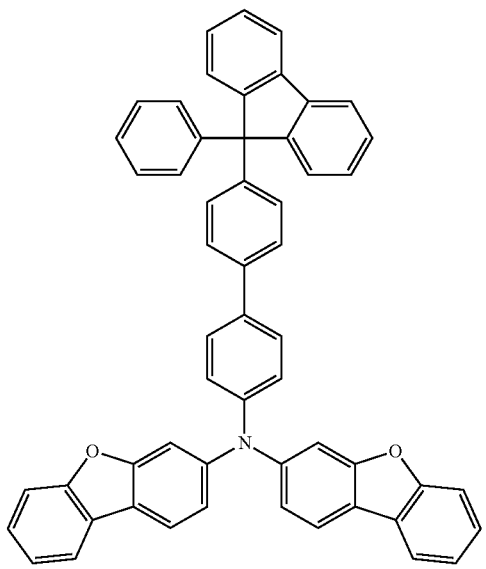

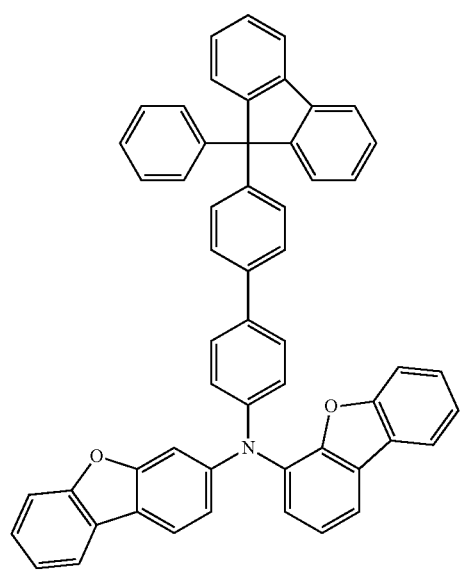
7
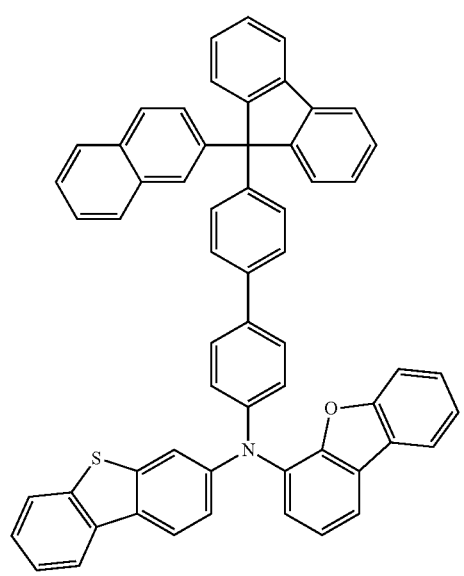
8
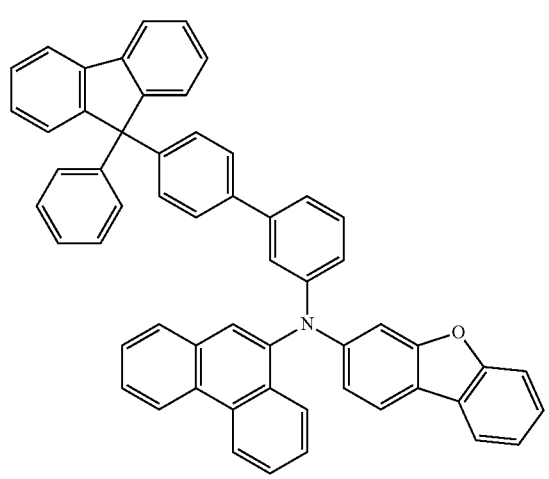
9
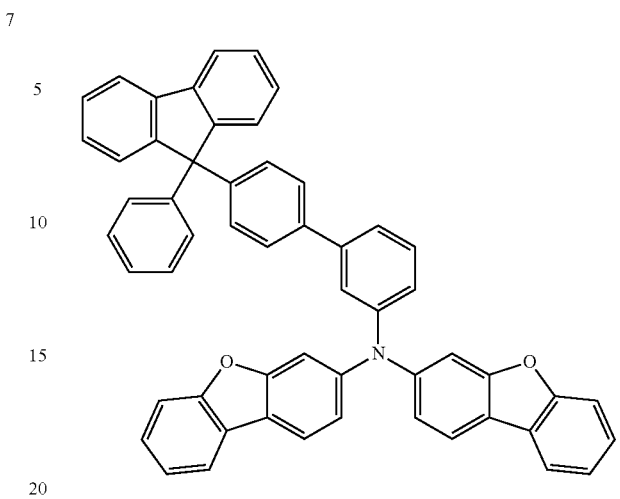
10
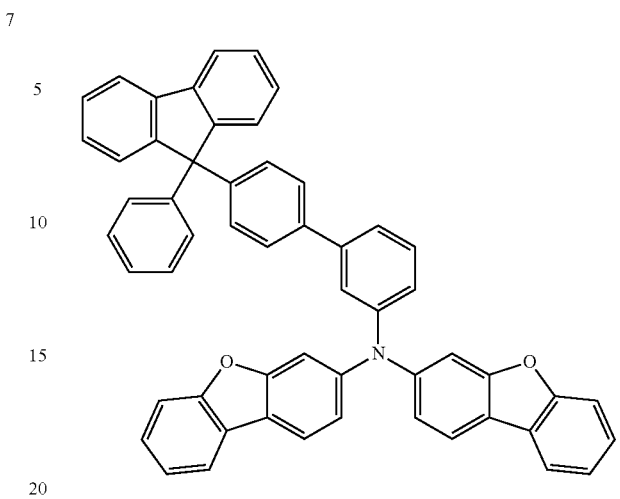
11
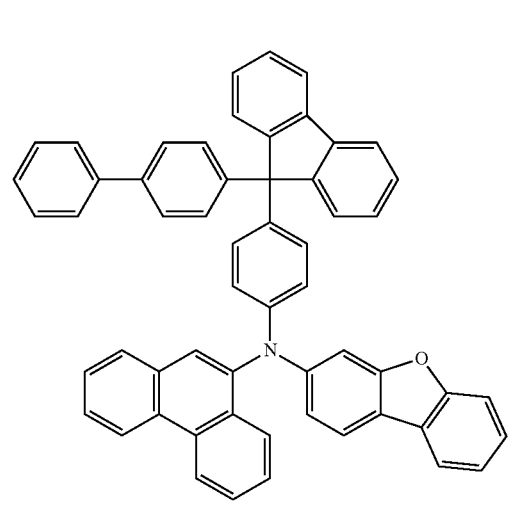
12

13
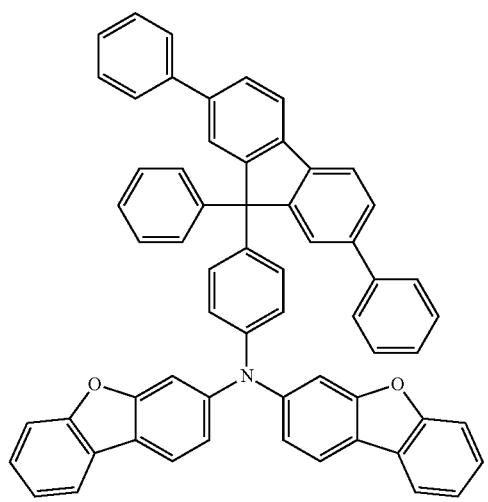
14
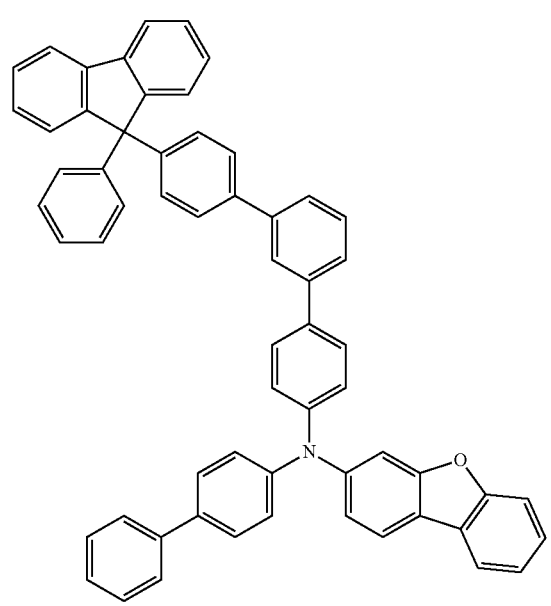
15
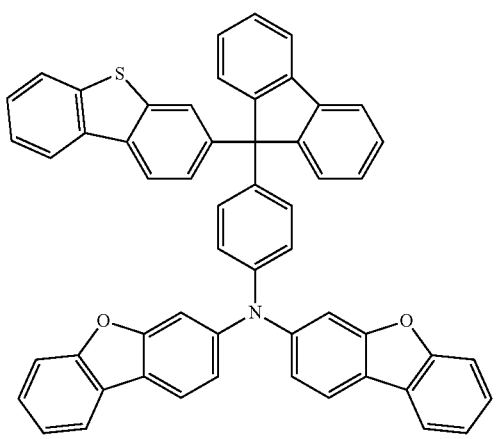
16
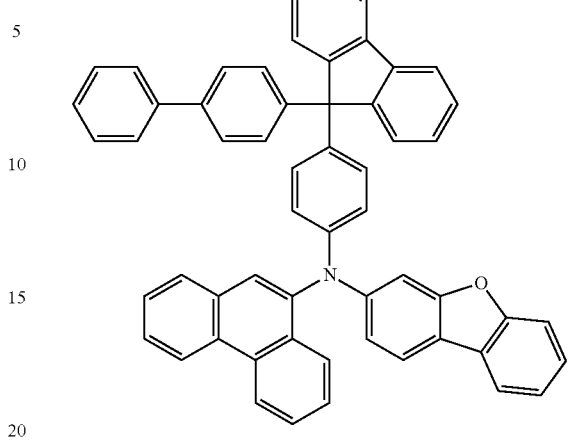
17
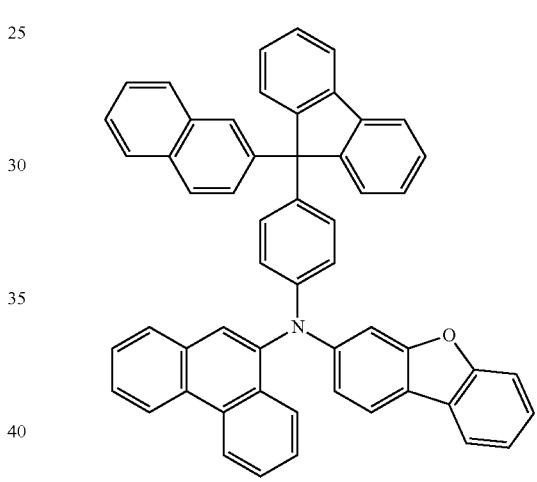
18
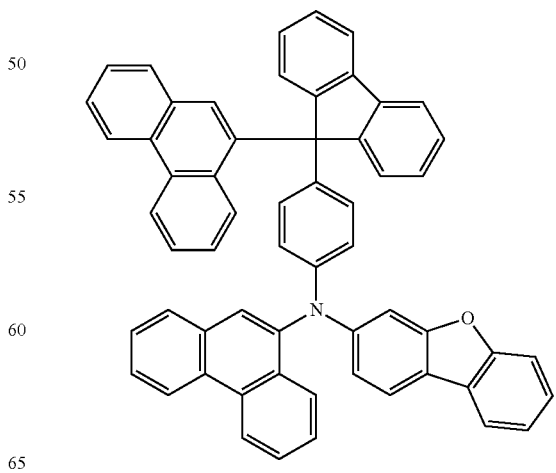

19
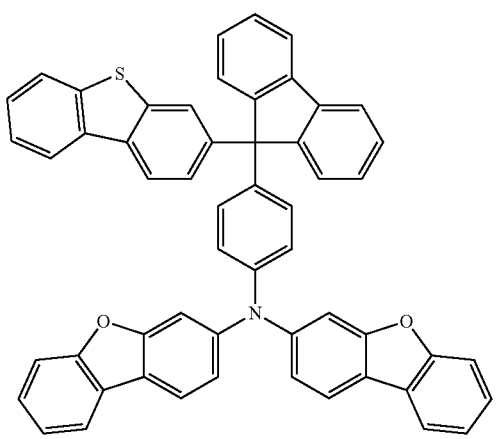
Formula 4
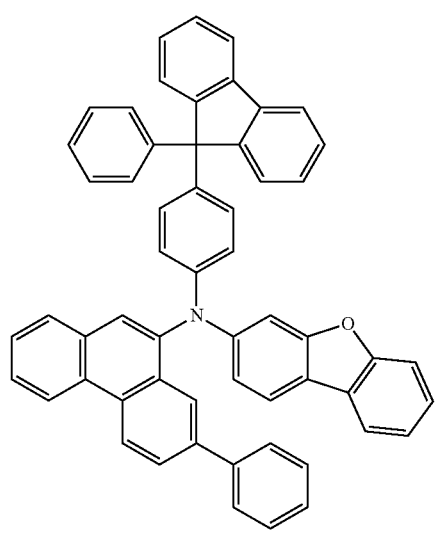
21
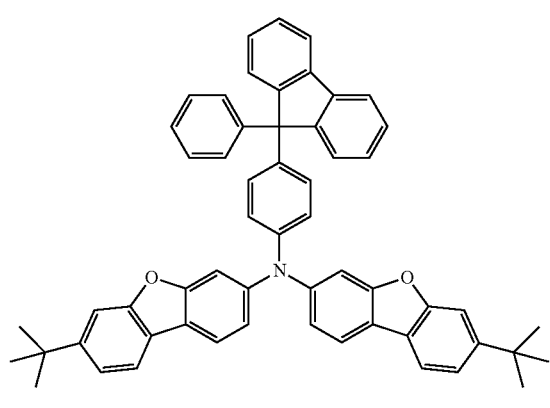
22
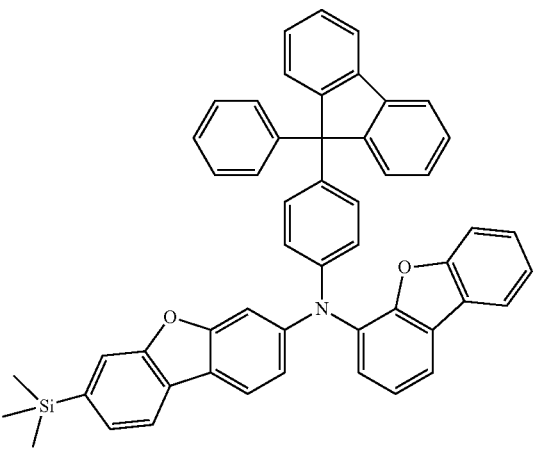
23
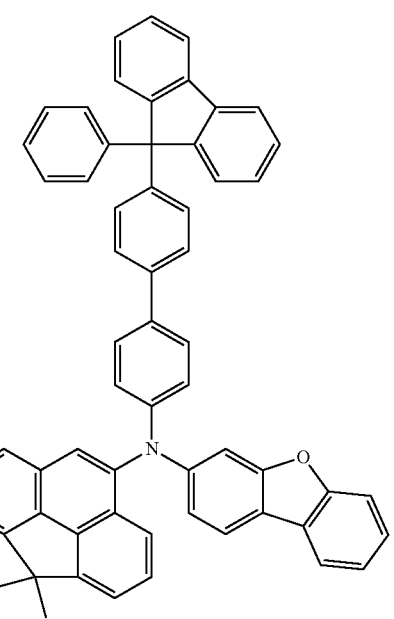
24

25
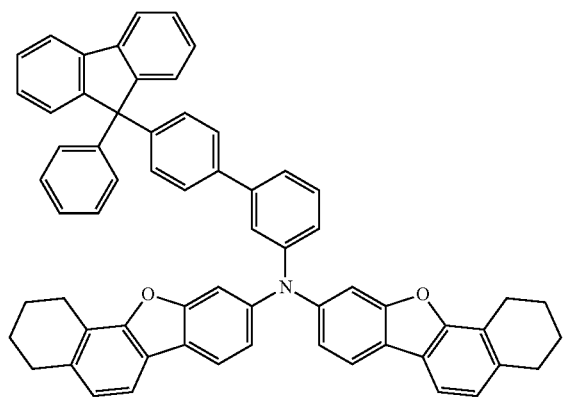
26
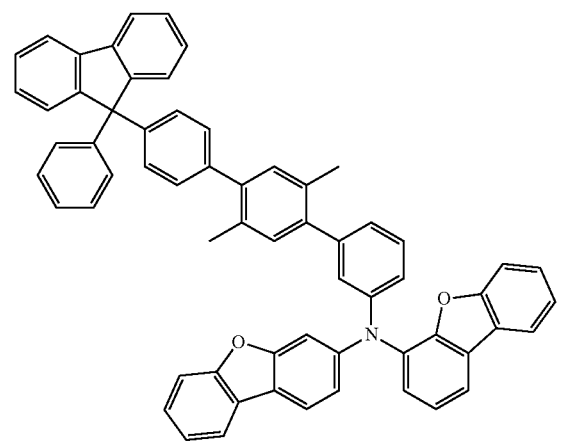
27
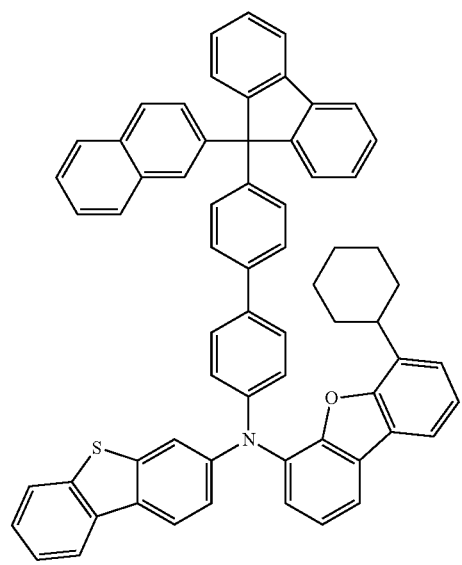
28
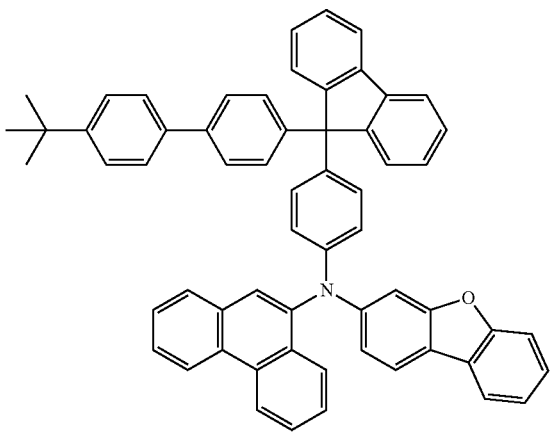
29
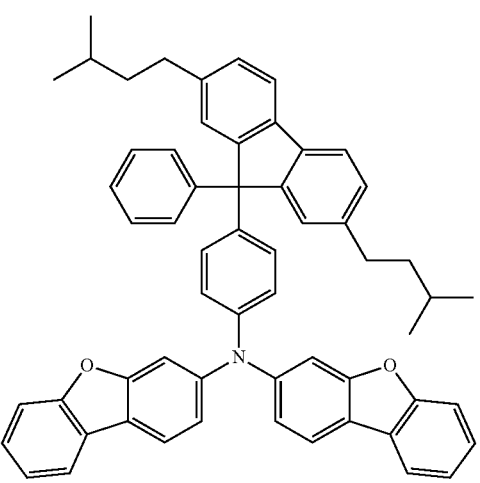
30
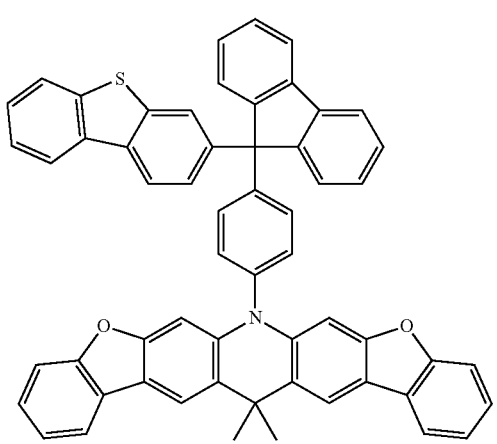

31
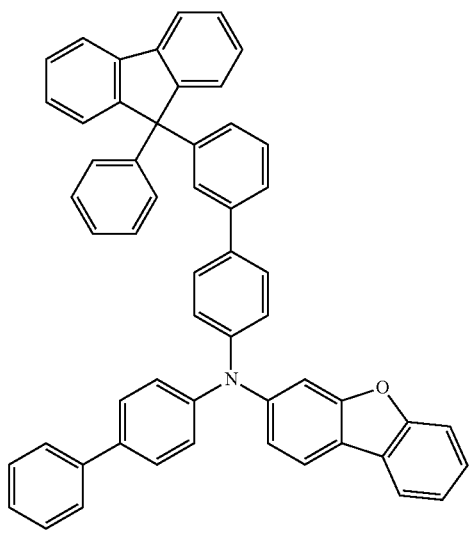
32
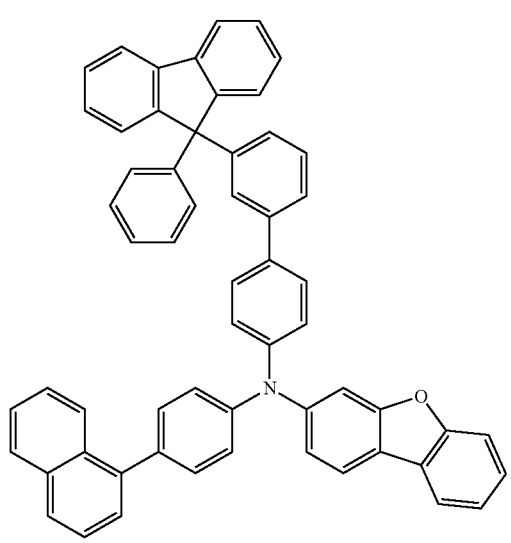
33
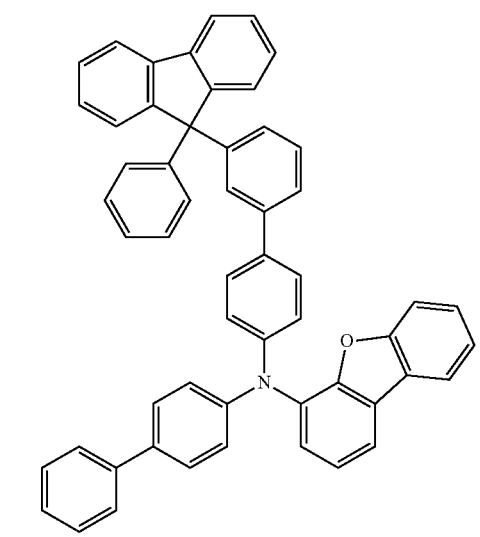
34
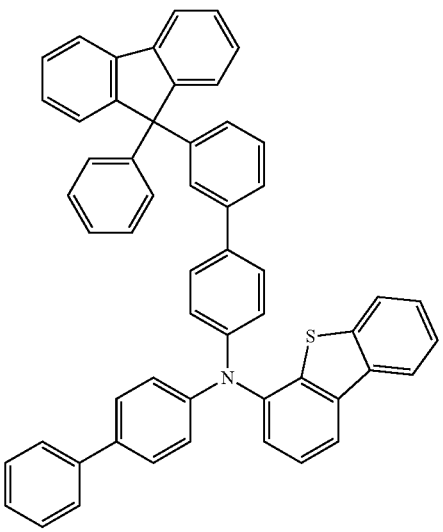
35
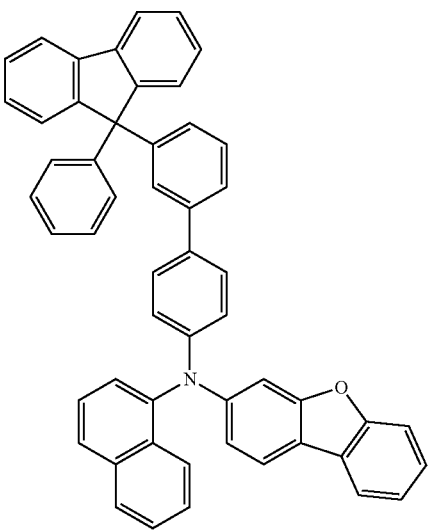
36
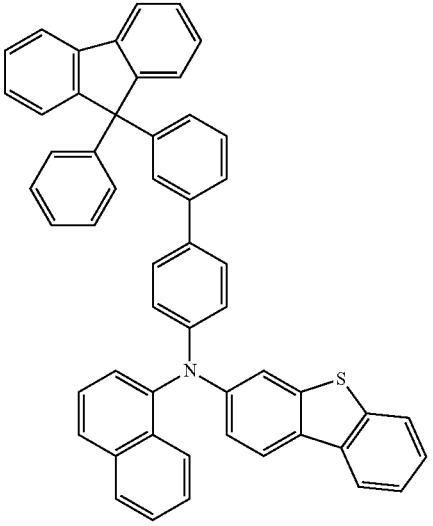

37
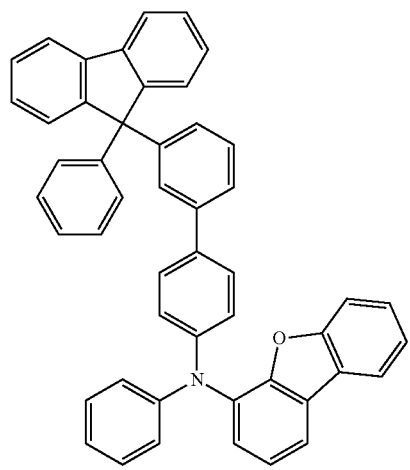
38
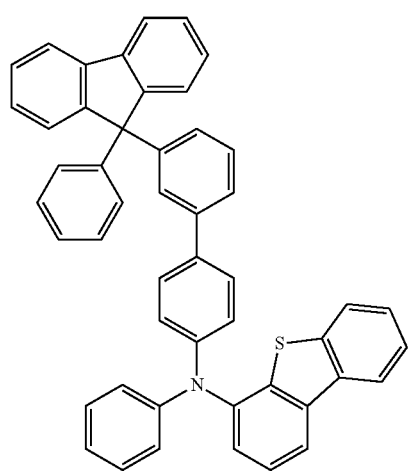
39
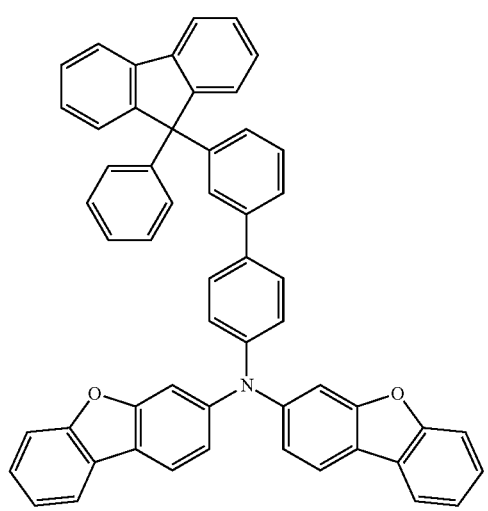
40
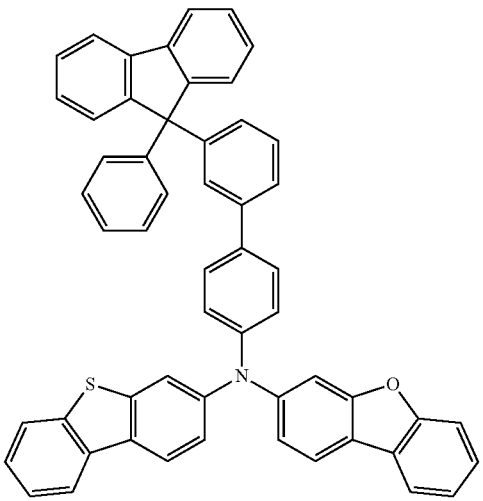
41
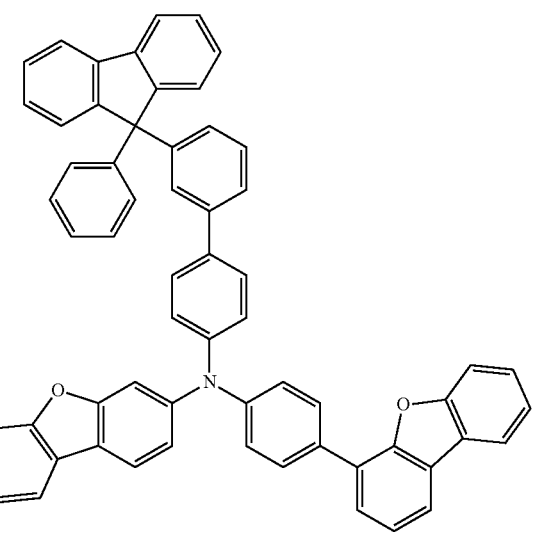
42
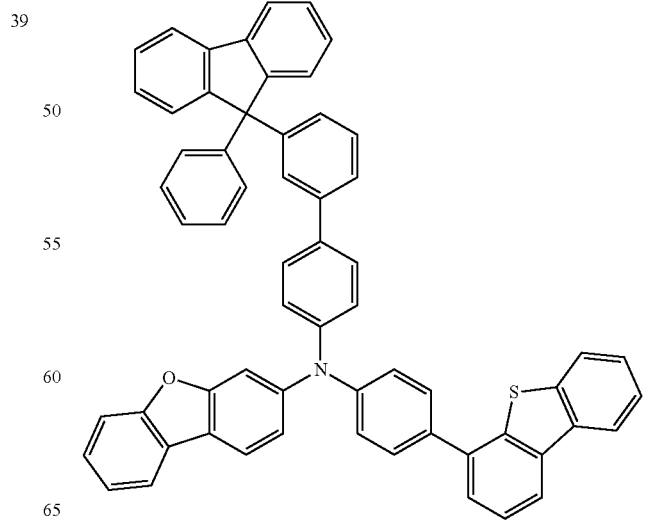

Formula 5
43
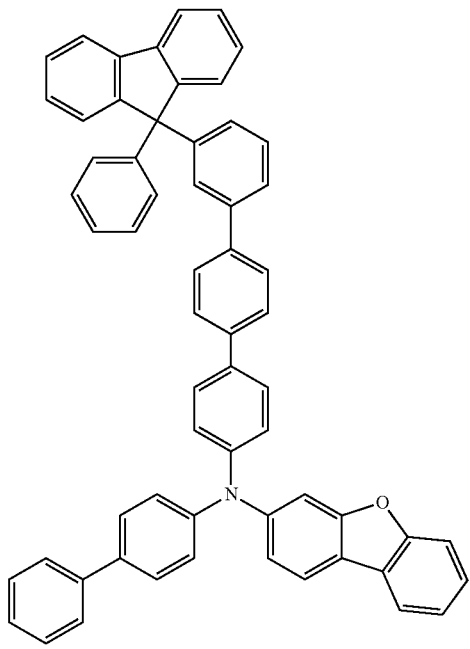
44
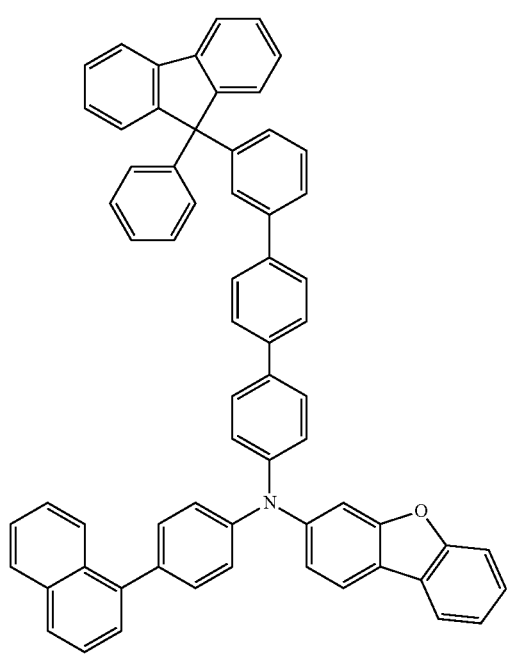
45
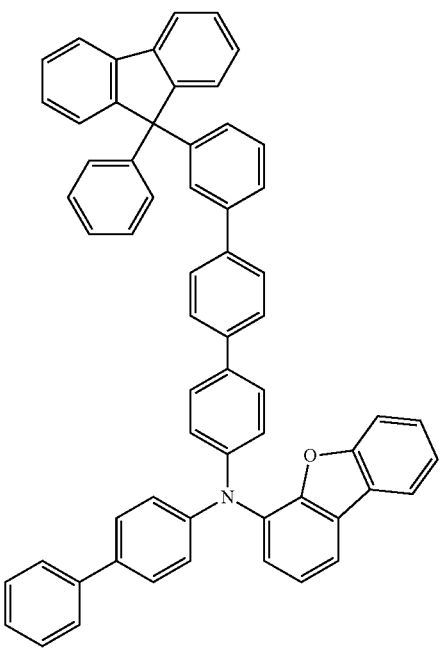
46
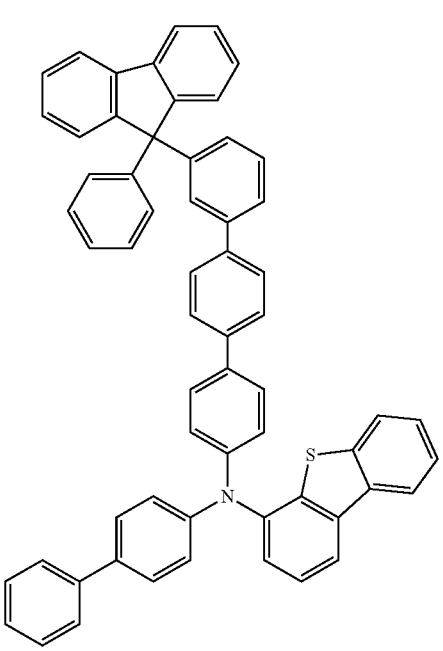

47
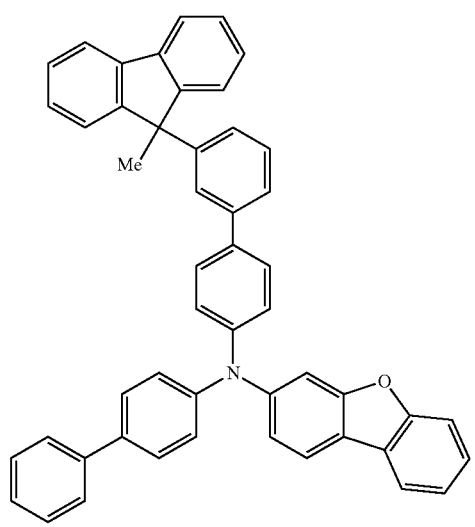
48
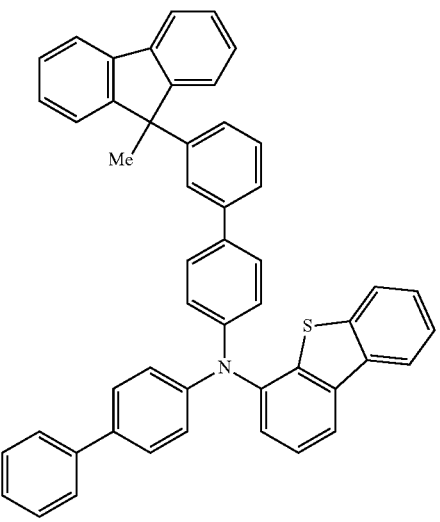
49
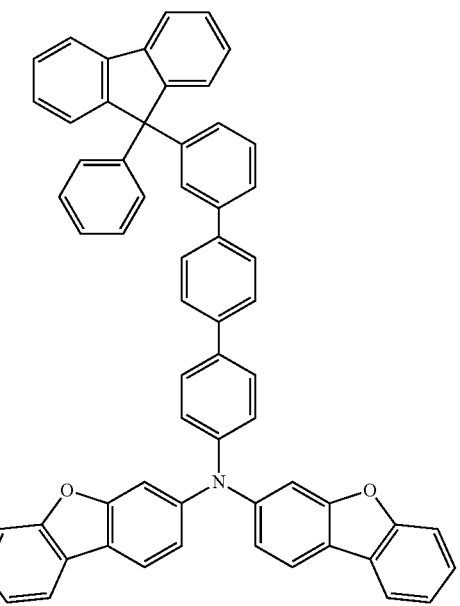
50
51

52

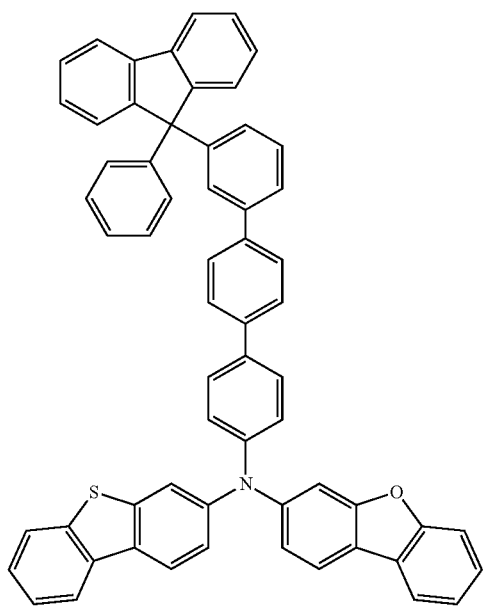

53

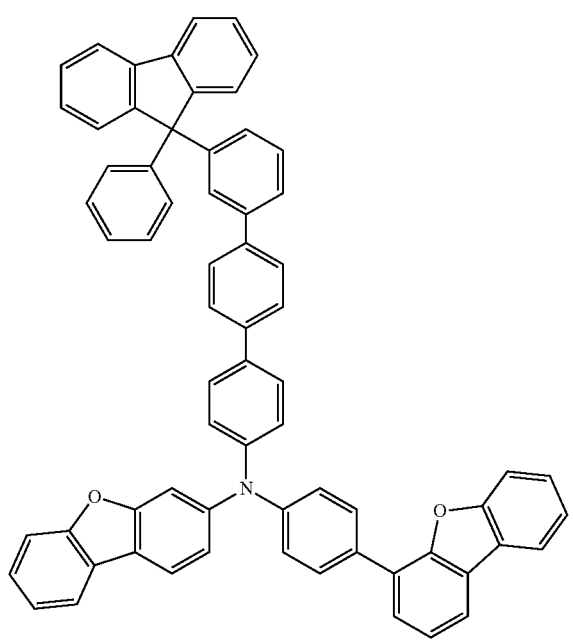

54

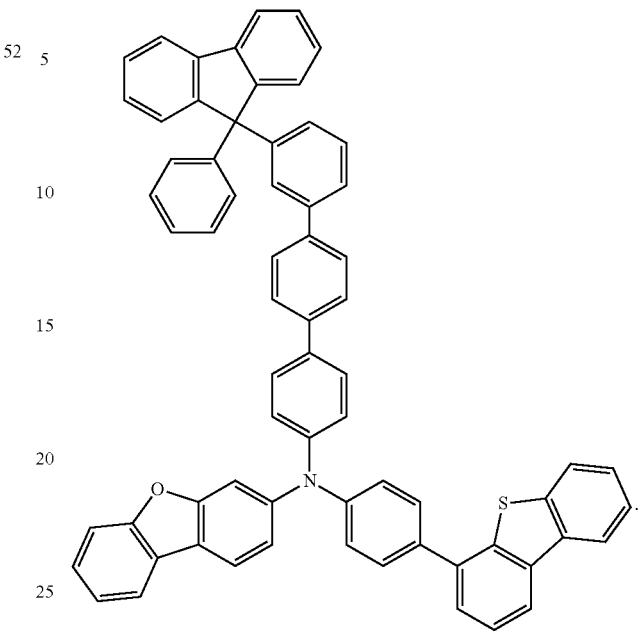

Hereinabove, the amine compound according to the present embodiments has been described in more detail.

In some embodiments, the amine compound according to the present embodiment includes an arylamino group in the molecular structure thereof, and is able to transport holes, and thus may be used as a hole transport material. Moreover, the amine compound according to the present embodiment has high electron resistance and electron blocking ability, and thus may prevent or reduce, for example, a hole transport layer from being deteriorated by invading electrons (e.g., by electrons leaking into the hole transport layer), and thus may prevent or reduce the electrons from diffusing into a hole injection layer or an anode. Therefore, the organic electroluminescent device of an embodiment which includes the amine compound according to the present embodiment (e.g., the amine compound of Formula 1) may have an improved device lifetime.

Organic Electroluminescent Device According to an Embodiment of the Inventive Concept Referring to drawing, a more detailed description will now be given of an organic electroluminescent device according to an embodiment which includes an amine compound represented by Formula 1. The drawing is a schematic cross-sectional view illustrating an example of an organic electroluminescent device according to an embodiment of the inventive concept.

As illustrated in the drawing, an organic electroluminescent device 100 according to the present embodiment includes a substrate 110, a first electrode 120 disposed (e.g., positioned) on the substrate 110, a hole injection layer 130 disposed on the first electrode 120, a hole transport layer 140 disposed on the hole injection layer 130, an emission layer 150 disposed on the hole transport layer 140, an electron transport layer 160 disposed on the emission layer 150, an electron injection layer 170 disposed on the electron transport layer 160, and a second electrode 180 disposed on the electron injection layer 170.

In some embodiments, the amine compound according to the present embodiment may be included, for example, in at least one selected from the hole injection layer 130 and the hole transport layer 140. In some embodiments, the amine compound according to the present embodiment may be included in both of the aforementioned layers. For example, the amine compound according to the present embodiment may be included in the hole transport layer 140 which is adjacent to the emission layer 150.

Each organic thin-film layer disposed (e.g., positioned) between the first electrode 120 and the second electrode 180 in the organic electroluminescent device 100 may be formed by one or more suitable methods such as deposition, etc.

Any substrate which is suitable for use in a general organic electroluminescent device may be used as the substrate 110. For example, the substrate 110 may be a glass substrate, a semiconductor substrate, a transparent plastic substrate, etc.

The first electrode 120 may be disposed on the substrate 110. For example, the first electrode 120 may be an anode. In some embodiments, the first electrode 120 may be formed as a transmissive electrode using a metal, an alloy, a conductive compound, etc., which have a large work function. In some embodiments, the first electrode 120 may be formed of indium tin oxide (ITO), indium zinc oxide (IZO), tin oxide ($SnO_2$), zinc oxide (ZnO), etc. which are transparent and have a good conductivity. In some embodiments, the first electrode 120 may be formed as a reflective electrode using magnesium (Mg), aluminum (Al), etc.

The hole injection layer 130 may be disposed on the first electrode 120. The hole injection layer 130 may facilitate hole injection from the first electrode 120. For example, the hole injection layer 130 may be formed to have a thickness of about 10 nm to about 150 nm.

The hole injection layer 130 may be formed of the amine compound according to the present embodiment, and may also (or alternatively) be formed of a suitable hole injection material. Non-limiting examples of the suitable material for forming the hole injection layer 130 may include, for example, triphenylamine-containing poly ether ketone (TPAPEK), 4-isopropyl-4'-methyldiphenyliodoniumtetrakis (pentafluorophenyl)borate (PPBI), N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4''-tris(3-methylphenylphenylamino) triphenylamine (m-MTDATA), N,N'-di(1-naphthyl)-N,N'-diphenylbenzidine (NPB), 4,4',4''-tris{N,N-diphenylamino}triphenylamine (TDATA), 4,4',4''-tris(N,N-2-naphthylphenylamino)triphenylamine (2-TNATA), polyaniline/dodecylbenzenesulfonic acid (PANI/DBSA), poly(3,4-ethylenedioxythiophene)/poly(4-styrenesulfonate (PEDOT/PSS), polyaniline/camphorsulfonic acid (PANI/CSA), polyaniline/poly(4-styrenesulfonate (PANI/PSS), etc.

The hole transport layer 140 may be disposed on the hole injection layer 130.

The hole transport layer 140 may include a hole transport material and may have a function of transporting holes. For example, the hole transport layer 140 may be formed to have a thickness of about 10 nm to about 150 nm. In some embodiments, the hole transport layer 140 may be formed of multiple layers (e.g., may have a multi-layer structure).

The hole transport layer 140 may be formed of the amine compound according to the embodiment of the present inventive concept. In the embodiments where the amine compound according to the present embodiment is included in the hole injection layer 130, the hole transport layer 140 may be formed of any suitable hole transport material. Non-limiting examples of the suitable hole transport material may include, for example, 1,1-bis[(di-4-tolylamino) phenyl]cyclohexane (TAPC); a carbazole derivative such as N-phenyl carbazole or polyvinyl carbazole; N,N'-bis(3-methylphenyl)-N,N'-diphenyl-[1,1-biphenyl]-4,4'-diamine (TPD); 4,4',4''-tris(N-carbazolyl)triphenylamine (TCTA); N,N'-di(1-naphthyl)-N,N'-diphenylbenzidine (NPB), etc.

The emission layer 150 may be disposed on the hole transport layer 140. The emission layer 150 is a layer which is capable of emitting light through fluorescence, phosphorescence, etc., and may be formed, for example, to have a thickness of about 10 nm to about 60 nm. Any suitable light-emitting material may be used as a light-emitting material of the emission layer 150. For example, light-emitting materials such as a fluoranthene derivative, a styryl derivative, a pyrene derivative, an arylacetylene derivative, a fluorene derivative, a perylene derivative, a chrysene derivative, etc., may be used. In some embodiments, the light-emitting material of the emission layer 150 may be selected from a styryl derivative, a pyrene derivative, a perylene derivative, and an anthracene derivative. For example, an anthracene derivative represented by the following Formula 6 may be used as the light-emitting material of the emission layer 150.

Formula 6

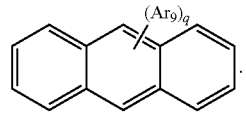

In the above Formula 6, $Ar^9$ is selected from hydrogen, deuterium, a substituted or unsubstituted alkyl group having 1 to 50 carbon atoms, a substituted or unsubstituted cycloalkyl group having 3 to 50 carbon atoms for forming a ring, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 carbon atoms for forming a ring, a substituted or unsubstituted arylthio group having 6 to 50 carbon atoms for forming a ring, a substituted or unsubstituted alkoxycarbonyl group having 2 to 50 carbon atoms for forming a ring, a substituted or unsubstituted aryl group having 6 to 50 carbon atoms for forming a ring, a substituted or unsubstituted silyl group having 5 to 50 carbon atoms for forming a ring, a carboxyl group, a halogen atom, a cyano group, a nitro group, and a hydroxyl group, and q may be an integer from 1 to 10.

In some embodiments, $Ar^9$ may be selected from a phenyl group, a biphenyl group, a terphenyl group, a naphthyl group, anthryl group, a phenanthryl group, a fluorenyl group, an indenyl group, a pyrenyl group, an acetonaphthenyl group, a fluoranthenyl group, a triphenylenyl group, a pyridyl group, a furanyl group, a pyranyl group, a thienyl group, a quinolyl group, a isoquinolyl group, a benzofuranyl group, a benzothienyl group, an indolyl group, a carbazolyl group, a benzoxazolyl group, a benzothiazolyl group, a quinoxalyl group, a pyrazolyl group, a dibenzofuranyl group, a dibenzothienyl group, etc. For example, $Ar^9$ may be a phenyl group, a biphenyl group, a terphenyl group, a fluorenyl group, a carbazolyl group, a dibenzofuranyl group, etc.

A compound represented by the above Formula 6 may include, for example, compounds a-1 to a-12 which are illustrated below and are collectively denoted as Formula 7.

However, the compound represented by Formula 6 is not limited to the following compounds.
Formula 7
a-1
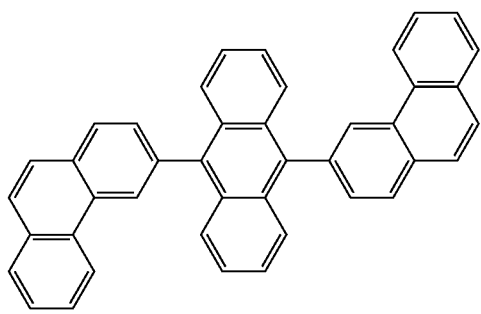
a-2
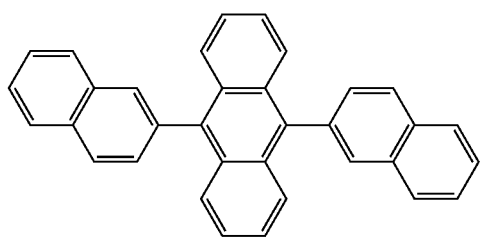
a-3
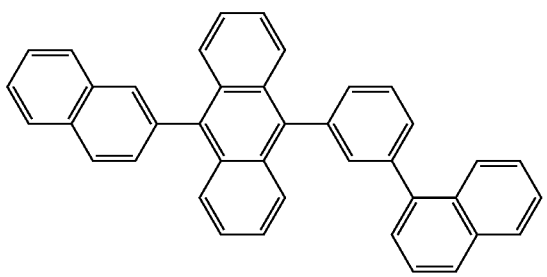
a-4
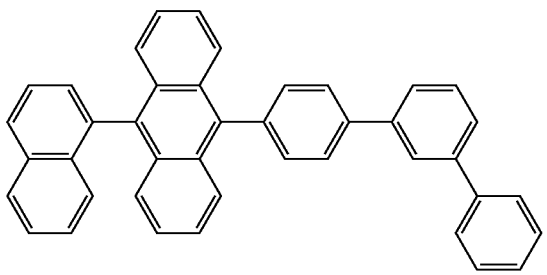
a-5
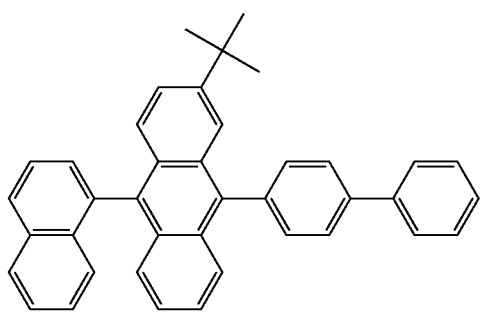
a-6
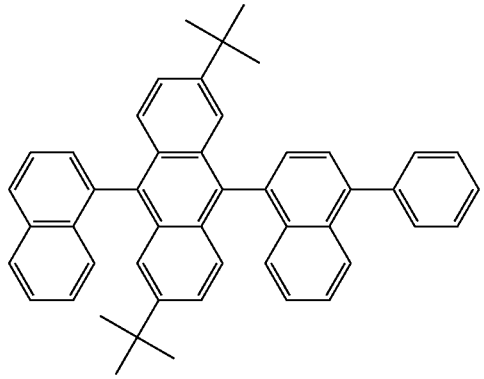
a-7
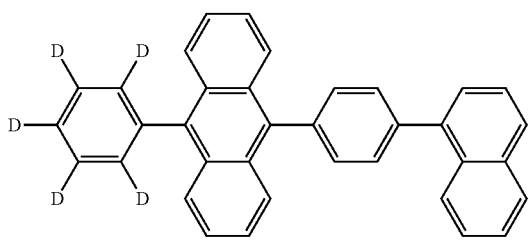
a-8
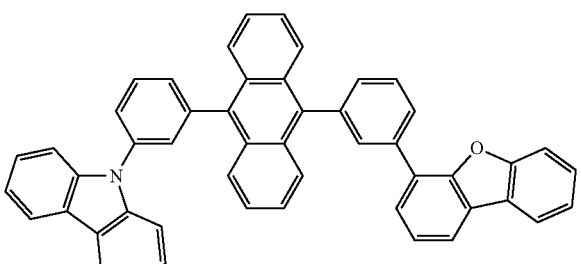
a-9
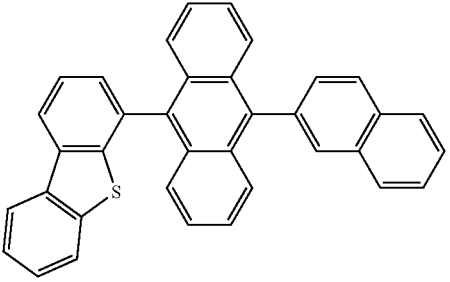
a-10
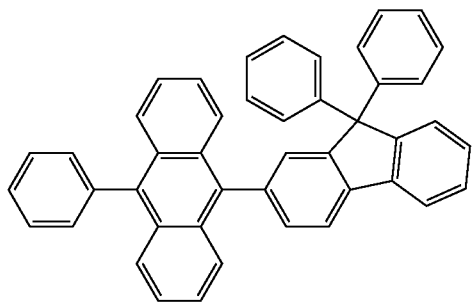

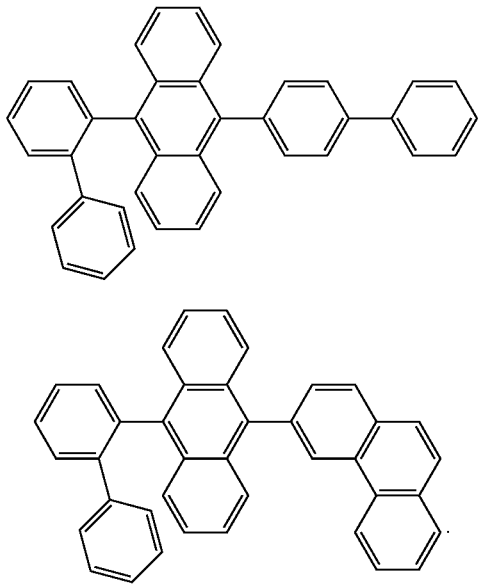

In some embodiments, the emission layer 150 may include, for example, a styryl derivative such as 1,4-bis[2-(3-N-ethylcarbazoryl)vinyl]benzene (BCzVB), 4-(di-p-tolylamino)-4'-[(di-p-tolylamino)styryl]stilbene (DPAVB), N-(4-((E)-2-(6-((E)-4-(diphenylamino)styryl)naphthalen-2-yl)vinyl)phenyl)-N-phenylbenzenamine (N-BDAVBi), etc.; a perylene derivative such as 2,5,8,11-tetra-t-butylperylene (TBPe); and a pyrene derivative such as 1,1-dipyrene,1,4-dipyrenylbenzene,1,4-bis(N,N-diphenylamino)pyrene as. However, materials included in the emission layer 150 are not limited to the above example compounds.

The electron transport layer 160 may be disposed on the emission layer 150. The electron transport layer 160 may be a layer in which an electron transport material which has a function of transporting electrons is included. For example, the electron transport layer 160 may be formed to have a thickness of about 15 nm to about 50 nm.

The electron transport layer 160 may be formed of any suitable electron transport material. Non-limiting examples of the suitable electron transport material may include, for example, tris(8-hydroxyquinolinato)aluminum (Alq3), a compound which has a nitrogen-containing aromatic ring, etc. A compound which has a nitrogen-containing aromatic ring may include, for example, a compound which has a pyridine ring, such as 1,3,5-tri[(3-pyridyl)-phen-3-yl]benzene; a compound which has a triazine ring, such as 2,4,6-tris(3'-(pyridin-3-yl)biphenyl-3-yl)-1,3,5-triazine; a compound which has a imidazole ring, such as 2-(4-(N-phenylbenzoim idazolyl-1-ylphenyl)-9,10-dinaphthylanthracene, etc.

The electron injection layer 170 may be disposed on the electron transport layer 160. The electron injection layer 170 may facilitate the injection of electrons from the second electrode 180. The electron injection layer 170 may be formed to have a thickness of about 0.3 nm to about 9 nm. Any material which is suitable for forming an electron injection layer may be used for the electron injection layer 170. For example, the electron injection layer 170 may be formed of a lithium (Li) complex (such as lithium 8-quinolinolato (Liq), lithium fluoride (LiF), etc.), sodium chloride (NaCl), cesium fluoride (CsF), lithium oxide ($Li_2O$), barium oxide (BaO), etc.

The second electrode 180 may be disposed on the electron injection layer 170. For example, the second electrode 180 may be a cathode, and may be formed as a reflective electrode using a metal, an alloy, a conductive compound, etc., which have a low work function. In some embodiments, the second electrode may be formed of, for example, a metal such as lithium (Li), magnesium (Mg), aluminum (Al), calcium (Ca), etc., or a mixture of metals such as aluminum-lithium (Al—Li), magnesium-indium (Mg—In), magnesium-silver (Mg—Ag), etc. The second electrode 180 may be formed as a transmissive electrode, using, for example, indium tin oxide, indium zinc oxide, etc.

Each of the above-described layers may be formed by appropriately selecting one or more suitable film forming methods, such as vacuum deposition, sputtering, various coating methods, etc., according to the material to be used in each layer.

Hereinabove, a description of an example structure of the organic electroluminescent device 100 according to the present embodiment has been provided. The organic electroluminescent device 100 including the amine compound of an embodiment of the present disclosure may have an improved emission lifetime.

However, the structure of the organic electroluminescent device 100 according to the present embodiment is not limited to the example structure as described above. The organic electroluminescent device 100 according to the present embodiment may also be manufactured using a variety of other suitable structures of an organic electroluminescent device. For example, the organic electroluminescent device 100 may exclude (e.g., may not include) at least one selected from a hole injection layer 130, an electron transport layer 160, and an electron injection layer 170. Alternatively, the organic electroluminescent device 100 may include an additional suitable layer, other than the layers described above. Each layer which is included in the organic electroluminescent device 100 may be formed as a single layer, or as multiple layers (e.g., as having a multi-layer structure).

In some embodiments, the organic electroluminescent device 100 may also include a hole blocking layer which is disposed (e.g., positioned) between the electron transport layer 160 and the emission layer 150 to prevent or reduce triplet excitons and holes from diffusing into the electron transport layer 160. The hole blocking layer may be formed, for example, of an oxadiazole derivative, a triazole derivative, a phenanthroline derivative, etc.

EXAMPLES

Hereinafter, an amine compound according to an embodiment of the inventive concept and an organic electroluminescent device including the amine compound will be described in more detail with reference to Examples and Comparative Examples. However, the Examples given below are provided for illustrative purposes only, and an amine compound according to the present embodiment and an organic electroluminescent device including the same are not limited to the foregoing Examples.

Synthesis of Amine Compound

First, a method of synthesizing an amine compound according to the present embodiment will be described by showing example methods of synthesizing Compounds 2, 6, 9 to 11, (selected from the compounds collectively denoted as Formula 3), and Compound 31 (selected from the compounds collectively denoted as Formula 4). However, below-described methods of synthesizing the amine compound are merely examples, and methods of synthesizing the amine compound according to embodiments of the inventive concept are not limited to examples given below.

Synthesis of Compound 2

Compound 2 (as an example of the amine compound according to the present embodiment) was synthesized according to the below Reaction Formula 1 (denoted as Formula 8).

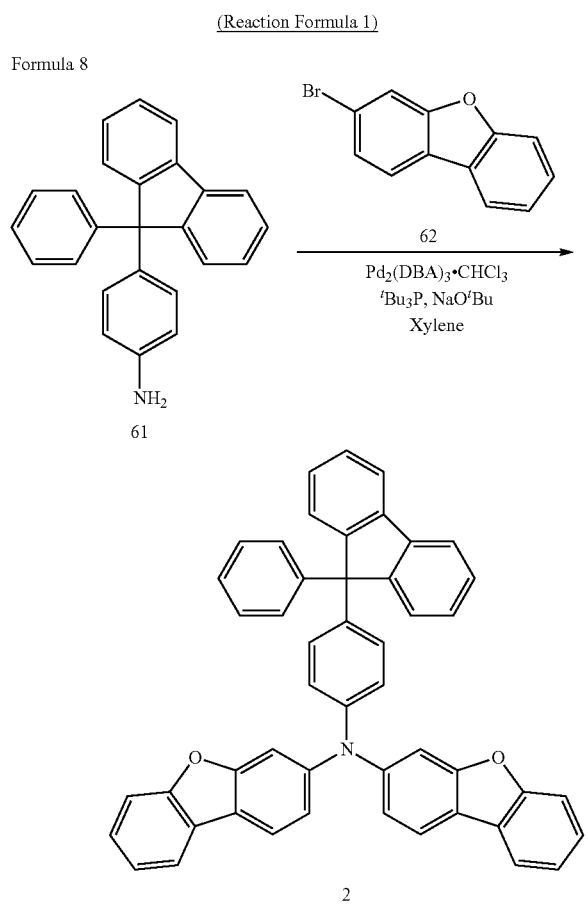

As shown in the above Reaction Formula 1, an arylamine compound, having a structure which is denoted as compound 61, may be undergo a reaction with a palladium (Pd) catalyst used to activate an aryl halide or a heteroaryl halide.

For example, after degassing a mixed solution containing 1.41 g (4.23 mmol) of 9-phenyl-9-(4-aminophenyl)fluorene (compound 61), 2.14 g (8.67 mmol) of 3-bromodibenzofuran (compound 62), 1.24 g (12.7 mmol) of sodium-tert-butoxide, 219 mg (0.211 mmol) of tris(dibenzilideneacetone)dipalladium·chloroform adduct, and 60 mL of anhydrous xylene, 159 L (0.254 mmol) of 1.6 M tri-t-butylphosphine solution was added to the mixed solution. After heating and refluxing the resultant mixture for 8 hours, the mixture was cooled and filtered. The filtered product was concentrated, and then purified through direct column chromatography to obtain 1.67 g (Yield 75%) of Compound 2 as a white powder.

The molecular weight of Compound 2 was measured using FAB-MS (Fast Atom Bombardment-Mass Spectrometry). The molecular weight as measured by FAB-MS was 665, which is equal to the molecular weight value calculated from the molecular formula, $C_{49}H_{31}NO_2$, of Compound 2, and thus the obtained product was confirmed to be Compound 2.

Synthesis of Compound 6

Compound 6 was synthesized through the same (or substantially the same) method as the synthetic method described in Reaction Formula 1 except that 9-phenyl-9-(4-aminobiphenyl)fluorene was used instead of 9-phenyl-9-(4-aminophenyl)fluorene (compound 61). The molecular weight of the resulting compound as measured (in substantially the same manner as Compound 2) by FAB-MS was 741. The measured molecular weight was equal to the molecular weight value calculated from the molecular formula, $C_{55}H_{35}NO_2$, and thus the obtained product was confirmed to be Compound 6.

Synthesis of Compound 9

Compound 9 was synthesized through the same (or substantially the same) method as the synthetic method described in Reaction Formula 1 except that 9-phenyl-9-(3'-amino-[1,1'-biphenyl]-4-yl)fluorene was used instead of 9-phenyl-9-(4-aminophenyl)fluorine (compound 61), and 3-bromodibenzofuran and 9-bromophenanthrene reacted twice in equal parts instead of 3-bromodibenzofuran. The molecular weight of the resulting compound as measured (in substantially the same manner as Compound 2) by FAB-MS was 751. The measured molecular weight was equal to the molecular weight value calculated from the molecular formula, $C_{57}H_{37}NO$, and thus the obtained product was confirmed to be Compound 9.

Synthesis of Compound 10

Compound 10 was synthesized through the same (or substantially the same) method as the synthetic method described in Reaction Formula 1 except that 9-phenyl-9-(3'-amino-[1,1'-biphenyl]-4-yl)fluorene was used instead of 9-phenyl-9-(4-aminophenyl)fluorine (compound 61). The molecular weight of the resulting compound as measured (in substantially the same manner as Compound 2) by FAB-MS was 741. The measured molecular weight was equal to the molecular weight value calculated from the molecular formula, $C_{55}H_{35}NO_2$, and thus the obtained product was confirmed to be Compound 10.

Synthesis of Compound 11

Compound 11 was synthesized through the same (or substantially the same) method as the synthetic method described in Reaction Formula 1 except that 9-phenyl-9-(3'-amino-[1,1'-biphenyl]-4-yl)fluorene was used instead of 9-phenyl-9-(4-aminophenyl)fluorene (compound 61), and 3-bromodibenzothiophene was used instead of 3-bromodibenzofuran. The molecular weight of the resulting compound as measured (in substantially the same manner as Compound 2) by FAB-MS was 773. The measured molecular weight was equal to the molecular weight value calculated from the molecular formula, $C_{55}H_{35}NS_2$, and thus the obtained product was confirmed to be Compound 11.

Synthesis of Compound 31

Compound 31 was synthesized through the same (or substantially the same) method as the synthetic method of Compound 9 except that 9-phenyl-9-(4'-amino-[1,1'-biphenyl]-3-yl)fluorene was used instead of 9-phenyl-9-(3'-amino-[1,1'-biphenyl]-4-yl)fluorene, and 4-bromo-(1,1'-biphenyl) was used instead of 9-bromophenanthrene. The molecular weight of the resulting compound as measured (in substantially the same manner as Compound 9) by FAB-MS was 727. The measured molecular weight was equal to the molecular weight value calculated from the molecular formula, $C_{55}H_{37}NO$, and thus the obtained product was confirmed to be Compound 31.

Here, using Suzuki coupling (which is a known synthesis method), 9-phenyl-9-(3-bromophenyl)fluorene and 1.1 equivalent of 4-(4,4,5,5-tetramethyl-1,3,2-dioxaborolan-2-yl)amine were reacted to synthesize 9-phenyl-9-(4'-amino-[1,1'-biphenyl]-3-yl)fluorene.

Manufacturing of Organic Electroluminescent Device Including Amine Compound

Next, organic electroluminescent devices including the amine compound according to the present embodiment as a hole transport material, were manufactured, through vacuum deposition, using the following acts, and was evaluated.

Example 1

First, surface treatment using ultra-violet radiation and ozone ($O_3$) was performed on an ITO-glass substrate which was subjected to patterning and cleaning. Here, the resulting ITO layer (a first electrode) on an ITO-glass substrate may have a thickness of about 150 nm. After the surface treatment, the substrate was cleaned, and the cleaned substrate was placed inside a deposition apparatus for forming organic films, and then a hole injection layer, a hole transport layer (HTL), an emission layer, and an electron transport layer were successively laminated on the substrate under a vacuum level of about $10^{-4}$ to about $10^{-5}$ Pa.

The hole injection layer was formed of 4,4',4"-tris(N,N-2-naphthylphenylamino)triphenylamine (2-TNATA) to have a thickness of about 60 nm. The hole transport layer was formed using Compound 2. In addition, the emission layer was formed using 9,10-di(2-naphthyl)anthracene (AND or ADN) as a host material and 2,5,8,11-tetra-t-butylperylene (TBP) as a dopant material, to have a layer thickness of about 25 nm. Moreover, a doping amount of the dopant material was about 3% (volume/volume) based on the volume of the host material. Furthermore, the electron transport layer was formed of Alq3 to have a layer thickness of about 25 nm.

Next, the substrate was transferred to the deposition apparatus for forming metal layers, and an electron injection layer and a second electrode were deposited thereon under a vacuum level of about $10^{-4}$ to $10^{-5}$ Pa, thus manufacturing an organic electroluminescent device. The electron injection layer was formed of lithium fluoride (LiF) to have a layer thickness of about 1 nm, and the second electrode was formed of aluminum (Al) to have a layer thickness of about 100 nm.

Example 2

An organic electroluminescent device was manufactured through the same (or substantially the same) method as the manufacturing method of Example 1 except a hole transport layer was formed of Compound 6.

Example 3

An organic electroluminescent device was manufactured through the same (or substantially the same) method as the manufacturing method of Example 1 except a hole transport layer was formed of Compound 9.

Example 4

An organic electroluminescent device was manufactured through the same (or substantially the same) method as the manufacturing method of Example 1 except that a hole transport layer was formed of Compound 10.

Example 5

An organic electroluminescent device was manufactured through the same (or substantially the same) method as the manufacturing method of Example 1 except that a hole transport layer was formed of Compound 11.

Example 6

An organic electroluminescent device was manufactured through the same (or substantially the same) method as the manufacturing method of Example 1 except that a hole transport layer was formed of Compound 31.

Comparative Example 1

An organic electroluminescent device was manufactured through the same (or substantially the same) method as the manufacturing method of Example 1 except that a hole transport layer was formed of Compound c1. Compound c1 differs from the amine compound according to the present embodiment (e.g., from Compound 6 of Example 2), in that in Compound c1, one of the covalent bonds which form a fluorene skeleton is not included.

Comparative Example 2

An organic electroluminescent device was manufactured through the same (or substantially the same) method as the manufacturing method of Example 1 except that a hole transport layer was formed of Compound c2. When compared to Compound 6, Compound c2 excludes (e.g., does not include) a dibenzoheterole ring, and is thus different from the amine compound according to the present embodiment.

Comparative Example 3

An organic electroluminescent device was manufactured through the same (or substantially the same) method as the manufacturing method of Example 1 except that a hole transport layer was formed of the following Compound c3. When compared with Compound 2, Compound c3 excludes (e.g., does not include) a dibenzoheterole ring, and is thus different from an amine compound according to an embodiment.

Formula 9 c1
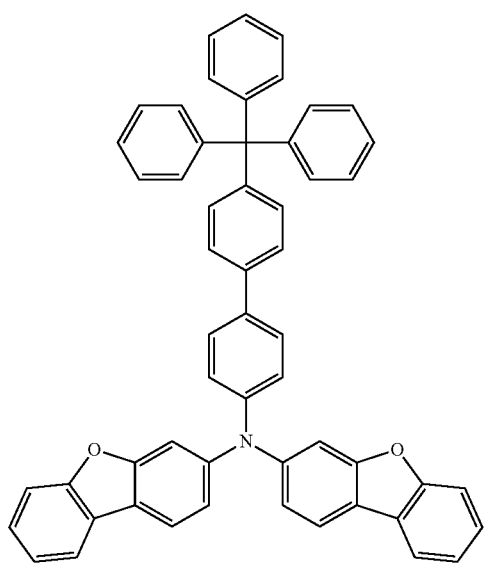

c2
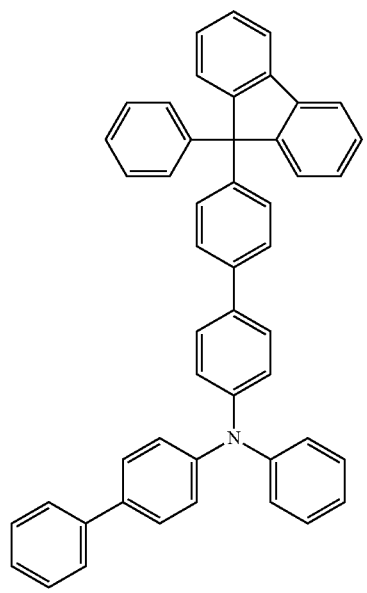

c3
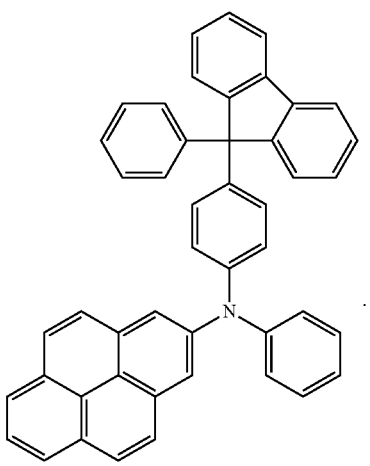

Evaluation Results

Evaluation results of the organic electroluminescent devices which were manufactured according to Examples 1 to 6 and Comparative Examples 1 to 3 are shown in the following Table 1. A C9920-11 luminance distribution characteristic measuring device (produced by HAMAMATSU Photonics) was used in the evaluation of the electroluminescent properties of the manufactured organic electroluminescent devices. The results which are shown in the below Table 1 were measured at a current density of about 10 mA/cm$^2$, and the emission lifetime was represented by time (LT50) necessary to decrease the luminance to half of the initial luminance of about 1,000 cd/m$^2$.

TABLE 1

| | HTL | Emission Lifetime LT50 (hrs) |
|---|---|---|
| Example 1 | Compound 2 | 1,500 |
| Example 2 | Compound 6 | 1,700 |
| Example 3 | Compound 9 | 2,200 |
| Example 4 | Compound 10 | 2,050 |
| Example 5 | Compound 11 | 2,000 |
| Example 6 | Compound 31 | 1,800 |
| Comparative Example 1 | Compound c1 | 1,000 |
| Comparative Example 2 | Compound c2 | 1,100 |
| Comparative Example 3 | Compound c3 | 1,050 |

Referring to the results shown in Table 1, when compared to the organic electroluminescent devices of Comparative Examples 1 to 3, it can be seen that the organic electroluminescent devices of Examples 1 to 6 have an improved emission lifetime.

For example, the organic electroluminescent devices of Examples 1 to 6, in which the amine compound according to the present embodiments was used in the hole transport layer (HTL), had an improved device lifetime when compared to the organic electroluminescent device of Comparative Example 1 in which Compound c1 (which has a structure in which one of the covalent bonds forming a fluorine skeleton is not included), was used in the hole transport layer. Moreover, Examples 1 to 6, in which the amine compound according to the present embodiments was used in the hole transport layer (HTL), had an improved device lifetime when compared to the organic electroluminescent devices of Comparative Examples 2 and 3, in which Compounds c2 and c3 (which excluded a dibenzoheterole ring) were used in the hole transport layer.

Furthermore, when comparing the organic electroluminescent devices of Examples 1 to 2 with those of Examples 3 to 6, Examples 3 to 6 showed a longer emission lifetime than Examples 1 to 2. This is at least in part due to the fact that in Compounds 2 and 6, used in the hole transport layer (HTL) in Examples 1 to 2, all of the phenylene groups connecting a fluorenyl group and an arylamino group connected the fluorenyl group and the arylamino group at a para position (either directly or through connecting phenylene group(s)). In contrast, in Compounds 9 to 11 and 31, used in the hole transport layers (HTL) in Examples 3 to 6, one of the phenylene groups connecting a fluorenyl group and an arylamino group connected the fluorenyl group and the arylamino group at a meta position (either directly or through connecting phenylene group(s)). Therefore, in the amine compound according to the present embodiment, at least one of the phenylene groups connecting a fluorenyl group and an arylamino group may connect the fluorenyl group and the arylamino group at a meta position (either directly or through connecting group(s)).

As described above, the amine compound according to the present embodiment includes a structure represented by the above-described Formula 1, and an organic electroluminescent device which uses the amine compound having such structure may have an improved emission lifetime. Therefore, the amine compound according to the present embodiment may be utilized as a material for use in an organic electroluminescent device and may be useful in various practical applications of an organic electroluminescent device.

According to one or more embodiments of the present inventive concept, an organic electroluminescent device using the amine compound of the present embodiments may have an improved emission lifetime.

As used herein, expressions such as "at least one of," "one of," "at least one selected from," and "one selected from," when preceding a list of elements, modify the entire list of elements and do not modify the individual elements of the list. Further, the use of "may" when describing embodiments of the present invention refers to "one or more embodiments of the present invention."

In addition, as used herein, the terms "use," "using," and "used" may be considered synonymous with the terms "utilize," "utilizing," and "utilized," respectively.

As used herein, the terms "substantially," "about," and similar terms are used as terms of approximation and not as terms of degree, and are intended to account for the inherent deviations in measured or calculated values that would be recognized by those of ordinary skill in the art.

Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein. All such ranges are intended to be inherently described in this specification such that amending to expressly recite any such subranges would comply with the requirements of 35 U.S.C. §112(a) and 35 U.S.C. §132(a).

The above-disclosed subject matter is to be considered illustrative and not restrictive, and the appended claims and equivalents thereof are intended to cover all such modifications, enhancements, and other embodiments, which fall within the true spirit and scope of the present inventive concept. Thus, to the maximum extent allowed by law, the scope of the present inventive concept is to be determined by the broadest permissible interpretation of the following claims and their equivalents, and shall not be restricted or limited by the foregoing detailed description.

What is claimed is:

1. An amine compound, represented by the following Formula 1:

Formula 1

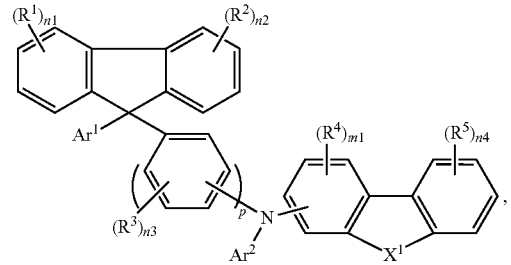

wherein, in the Formula 1,
$X^1$ is O or S;
$Ar^1$ and $Ar^2$ are each independently selected from a substituted or unsubstituted aryl group having 6 to 30 carbon atoms for forming a ring and a substituted or unsubstituted heteroaryl group having 2 to 30 carbon atoms for forming a ring;
$R^1$, $R^2$, $R^4$, and $R^5$ are each independently selected from a substituted or unsubstituted alkyl group having 1 to 10 carbon atoms, a substituted or unsubstituted cycloalkyl group having 5 to 10 carbon atoms for forming a ring, a substituted or unsubstituted aryl group having 6 to 20 carbon atoms for forming a ring, and a 5- to 7-membered ring structure obtained through bonding of any adjacent substituents;
$R^3$ is a substituted or unsubstituted alkyl group having 1 to 10 carbon atoms;
n1 to n4 are each independently an integer selected from 0 to 4;
m1 is an integer selected from 0 to 3; and
p is an integer selected from 1 to 3,
wherein at least one of the p number of phenylene groups connecting a flourenyl group and an arylamio group connects the flourenyl group and the arylamino group at a meta position.

2. The amine compound of claim 1, wherein:
the $Ar^1$ is a substituted or unsubstituted aryl group or a substituted or unsubstituted heteroaryl group, each independently obtained through 2- or 3-ring condensation of any of 5- to 6-membered aromatic and heteroaromatic rings.

3. The amine compound of claim 1, wherein:
the $Ar^2$ is a substituted or unsubstituted aryl group or a substituted or unsubstituted heteroaryl group, each independently obtained through 2- or 3-ring condensation of any of 5- to 6-membered aromatic and heteroaromatic rings.

4. The amine compound of claim 3, wherein
the $Ar^2$ is represented by the following Formula 2:

Formula 2

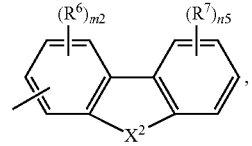

wherein, in Formula 2,

X² is O or S;

R⁶ and R⁷ are each independently selected from a substituted or unsubstituted alkyl group having 1 to 10 carbon atoms, a substituted or unsubstituted cycloalkyl group having 5 to 10 carbon atoms for forming a ring, a substituted or unsubstituted aryl group having 6 to 20 carbon atoms for forming a ring, and a 5- to 7-membered ring structure obtained through bonding of any adjacent substituents;

n5 is an integer selected from 0 to 4;

m2 is an integer selected from 0 to 3.

5. The amine compound of claim 1, wherein the amine compound represented by the above Formula 1 is selected from the group consisting of Compounds 1 to 19 and collectively denoted as Formula 3:

Formula 3

1
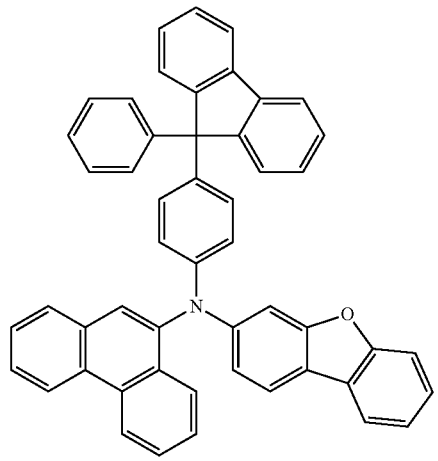

2
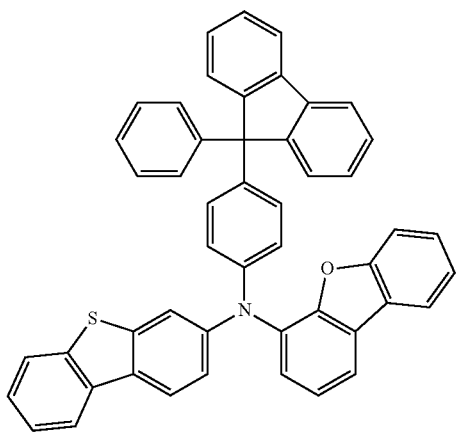

3
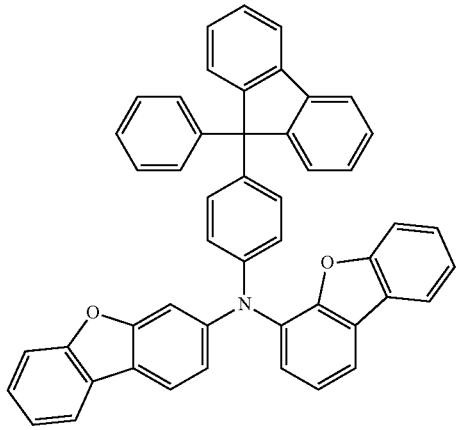

4
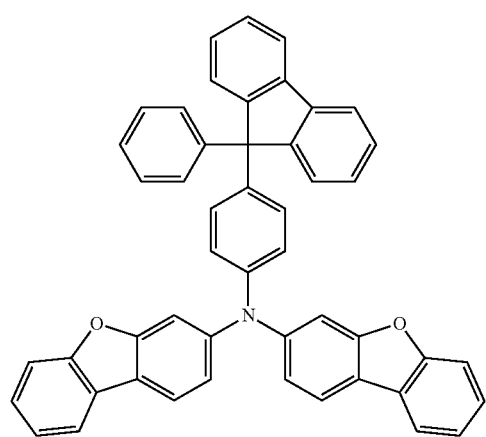

5
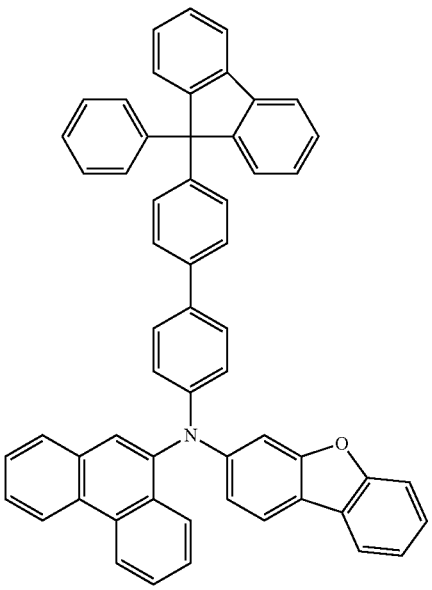

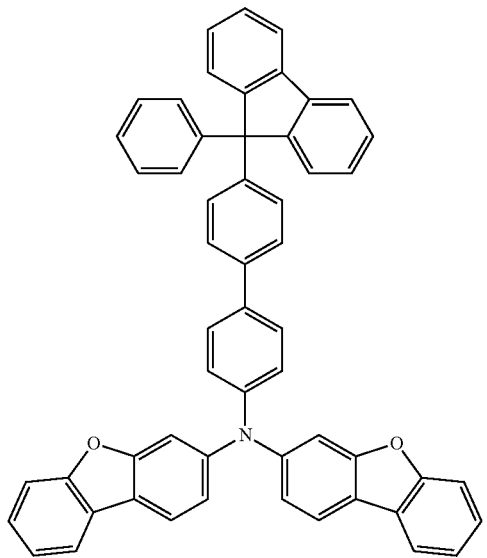
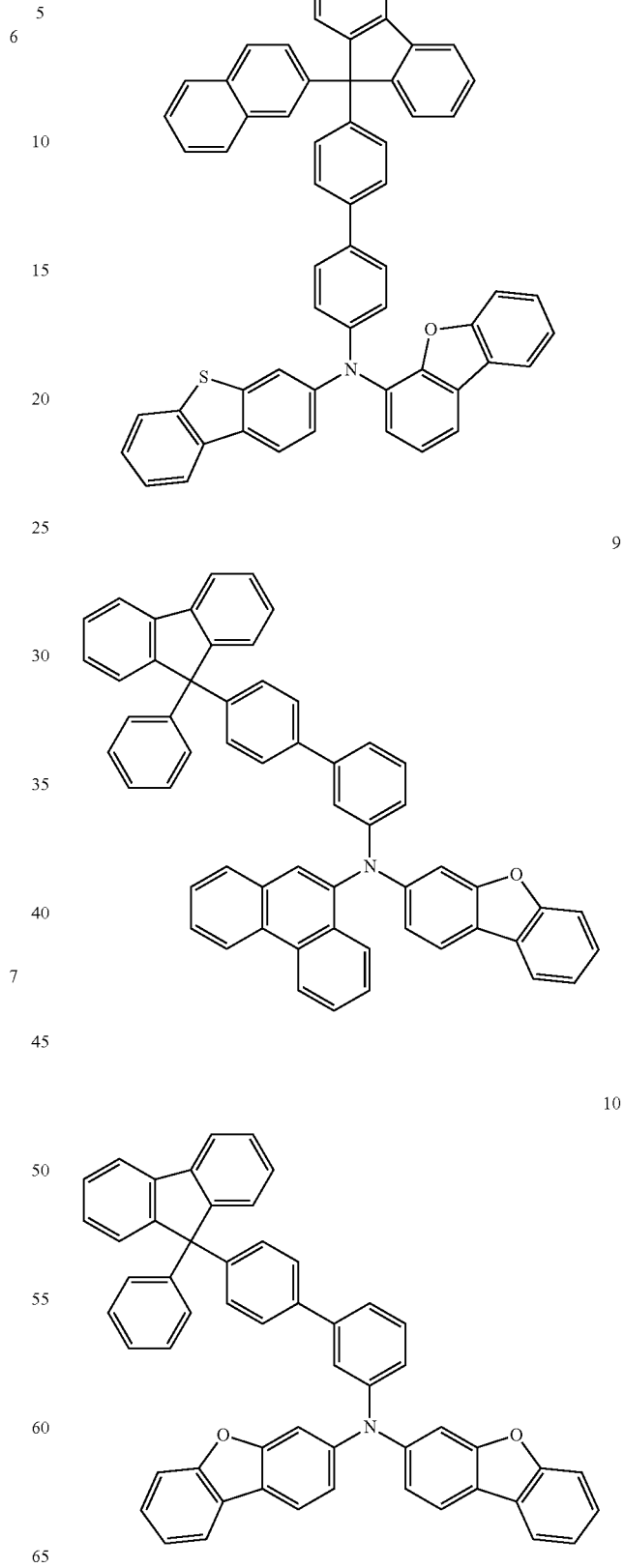

11
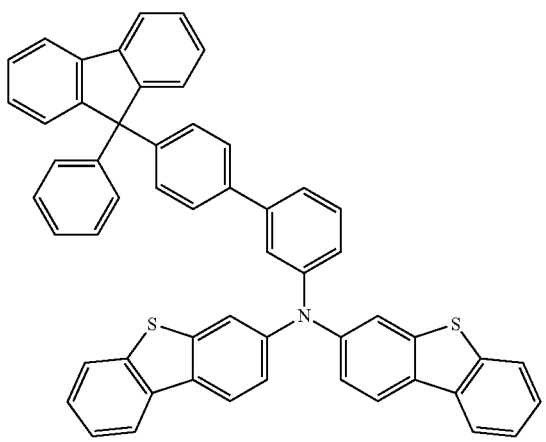
12
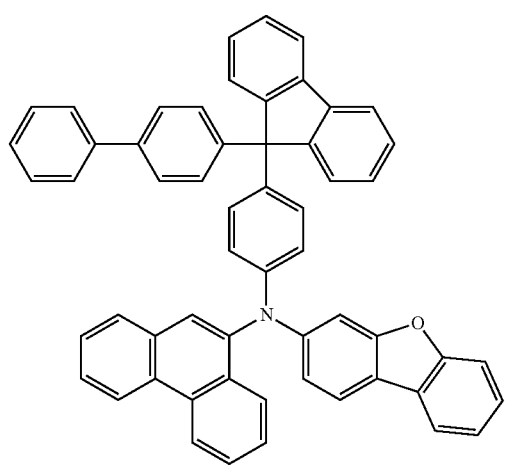
13
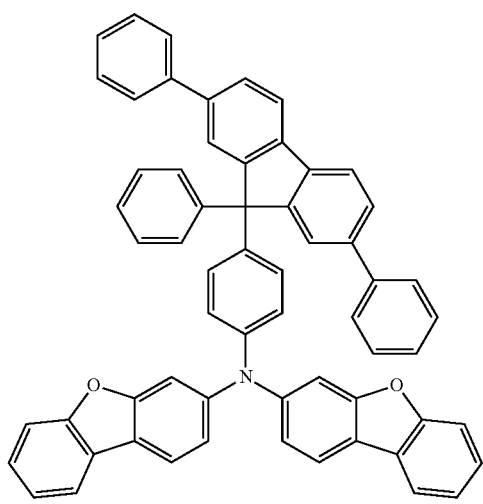
14
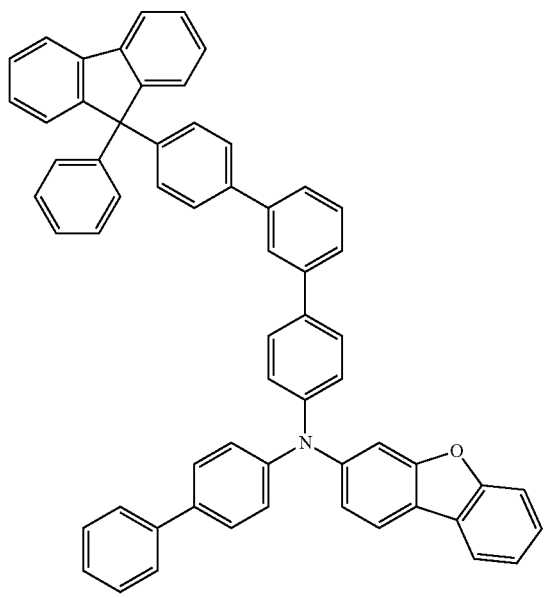
15
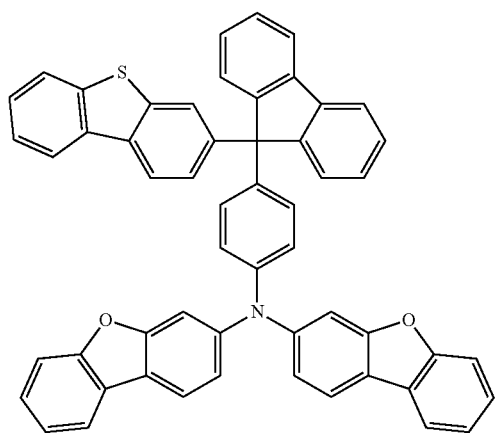
16
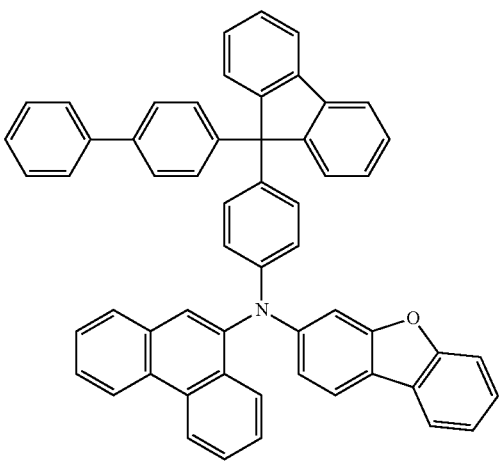

17
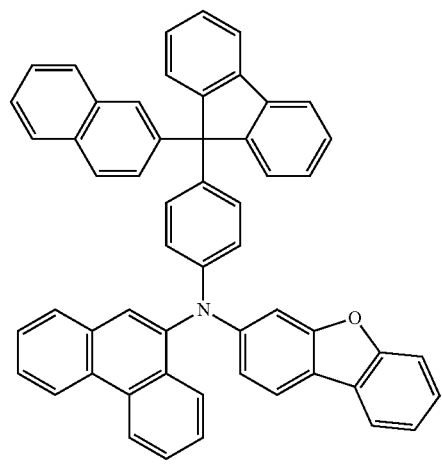
18
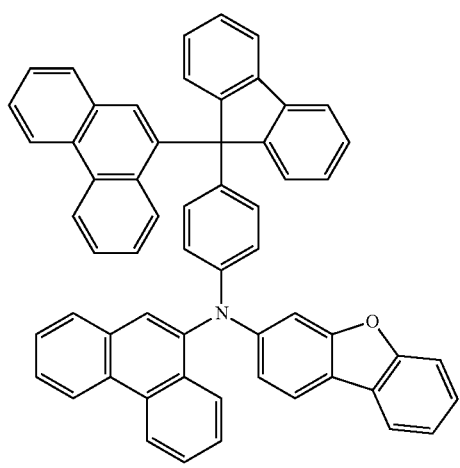
19
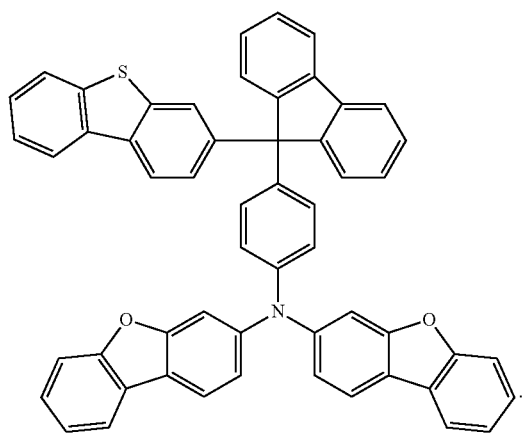
Formula 4
20
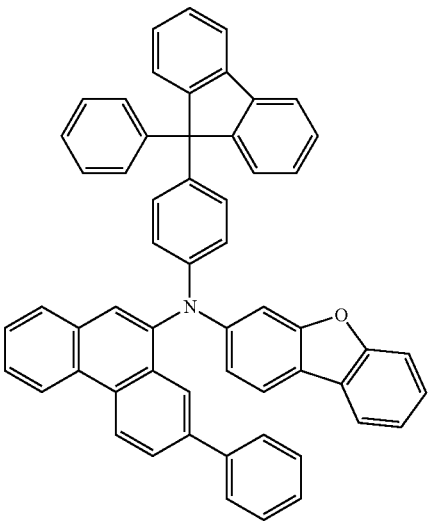
21
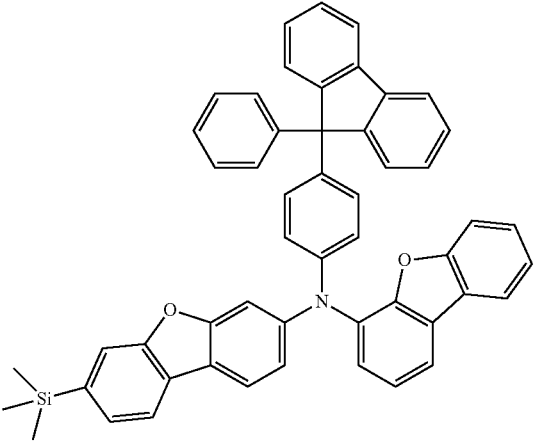
22
6. The amine compound of claim 1, wherein the amine compound represented by the above Formula 1 is selected from the group consisting of Compounds 20 to 42 and collectively denoted as Formula 4:

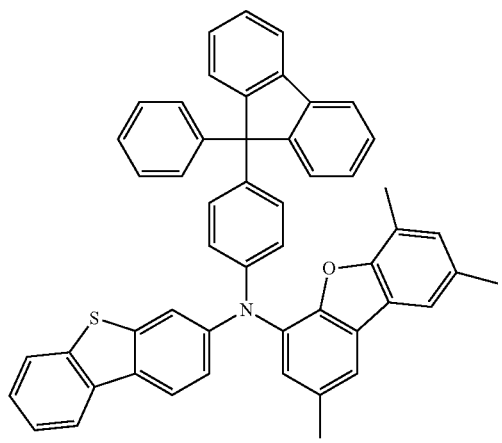
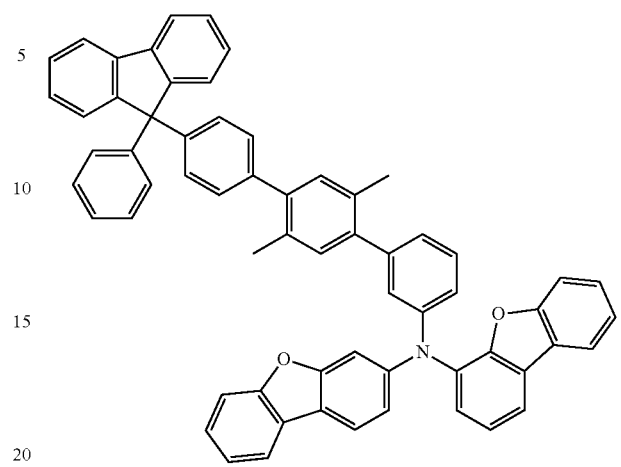
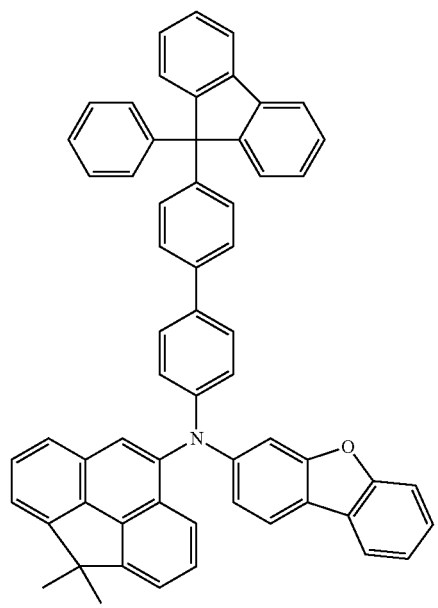
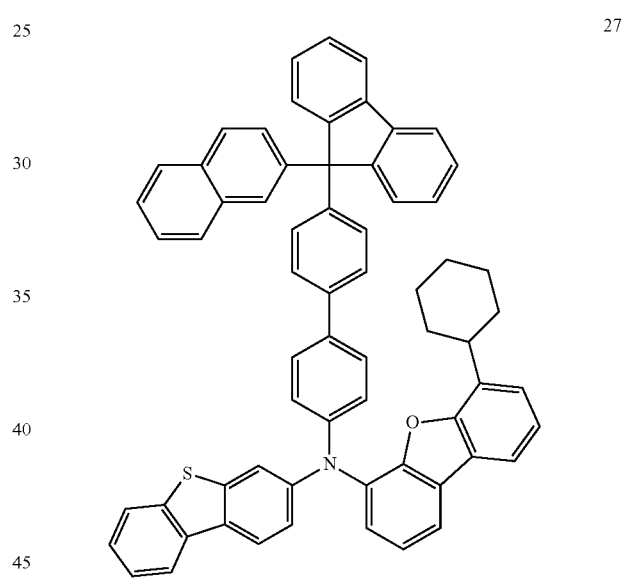
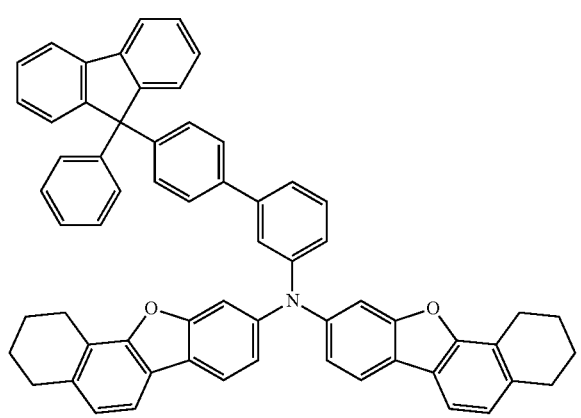
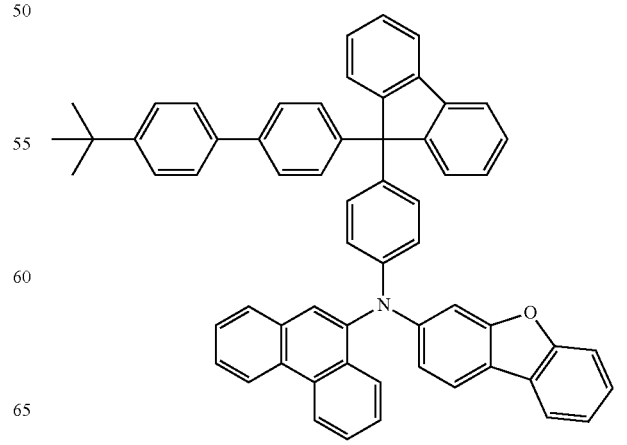

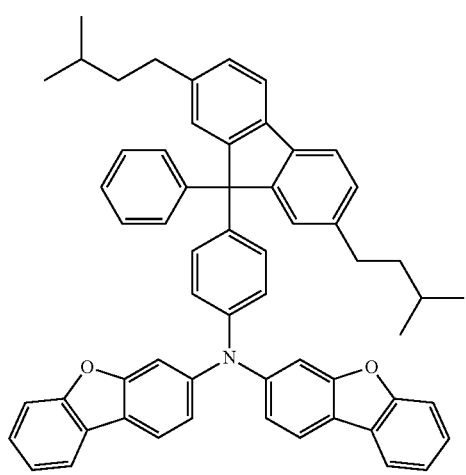
29
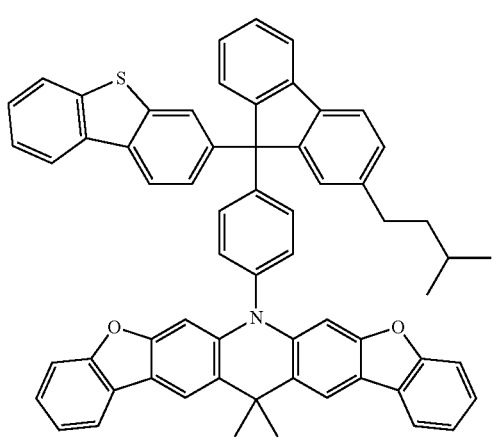
30
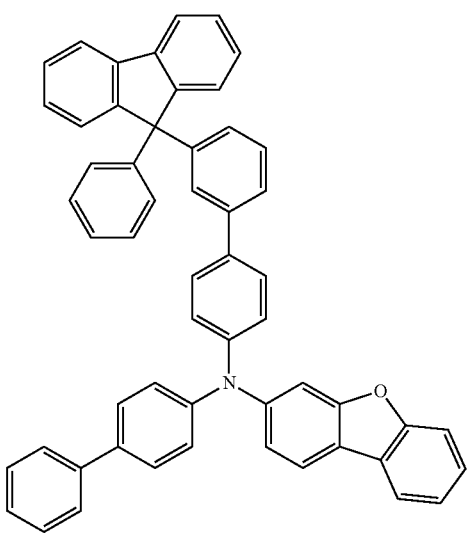
31
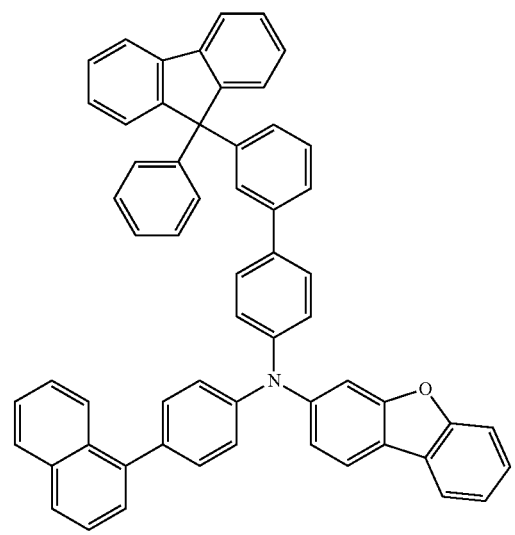
32
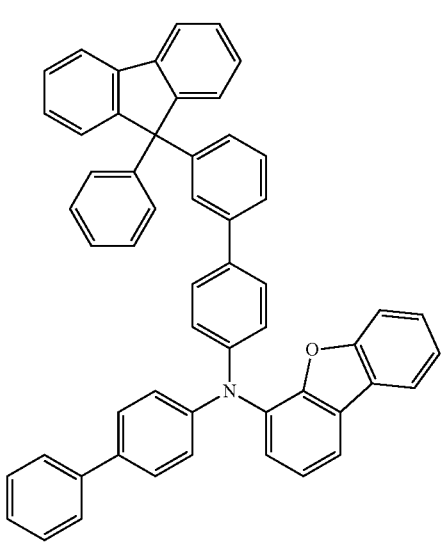
33
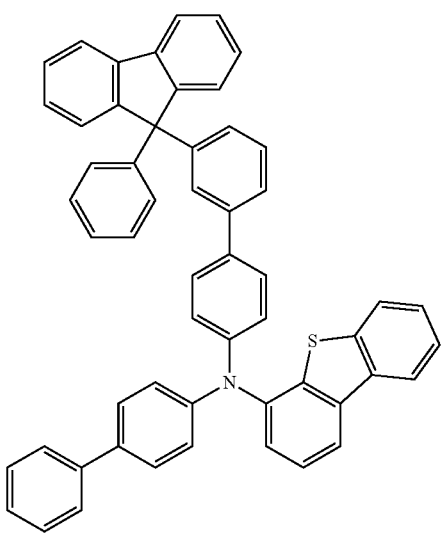
34

35
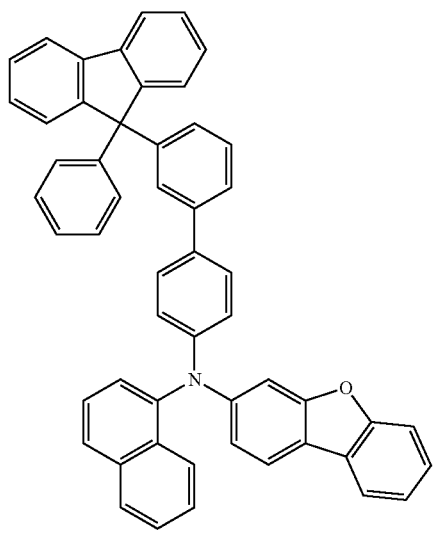
36
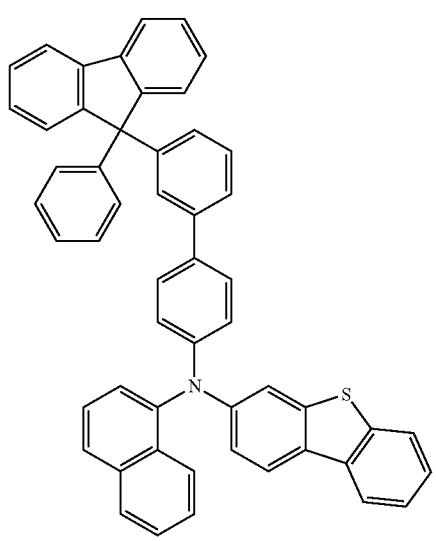
37
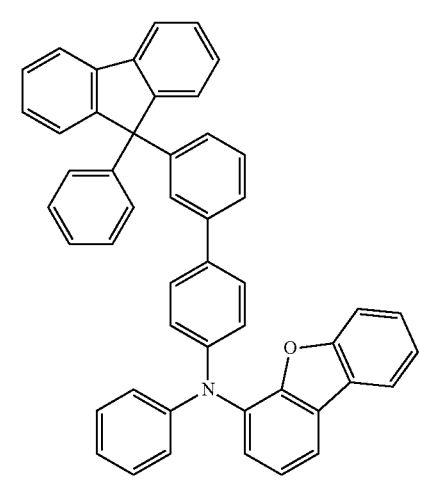
38
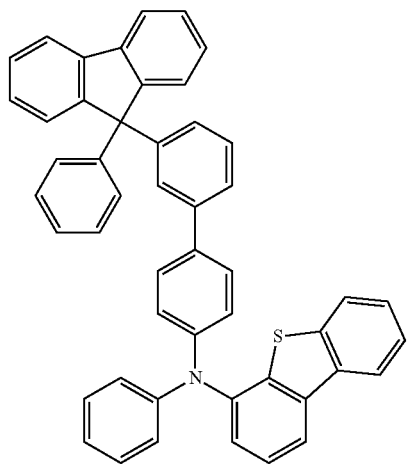
39
40
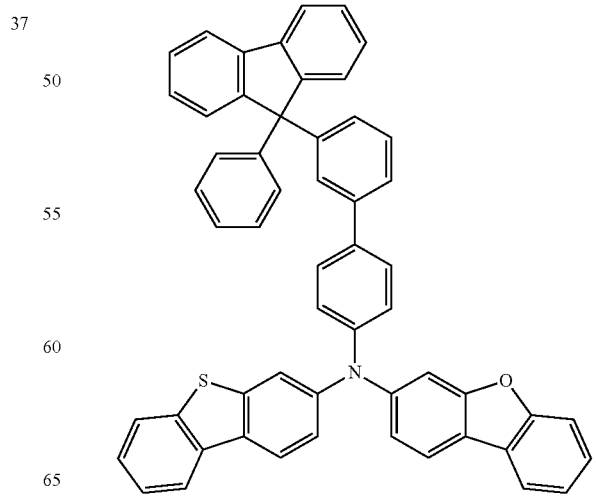

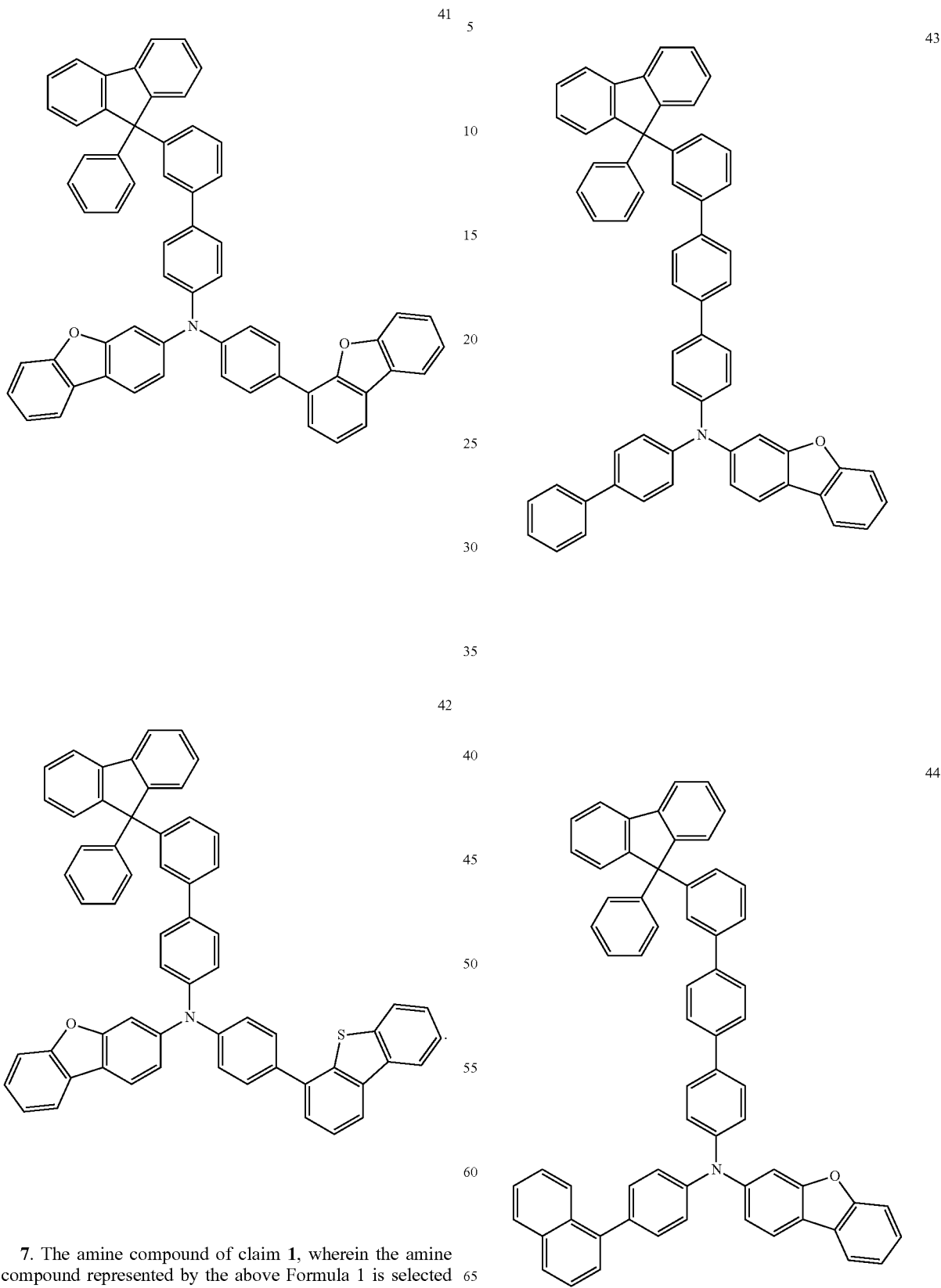
Formula 5
7. The amine compound of claim 1, wherein the amine compound represented by the above Formula 1 is selected from the group consisting of Compounds 43 to 54 and collectively denoted as Formula 5:

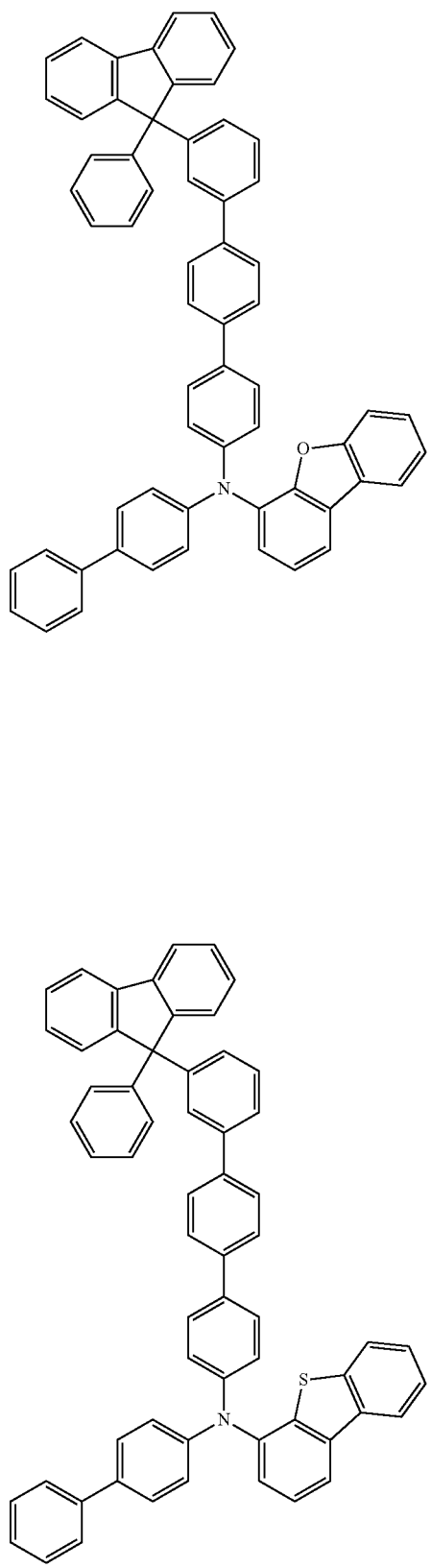
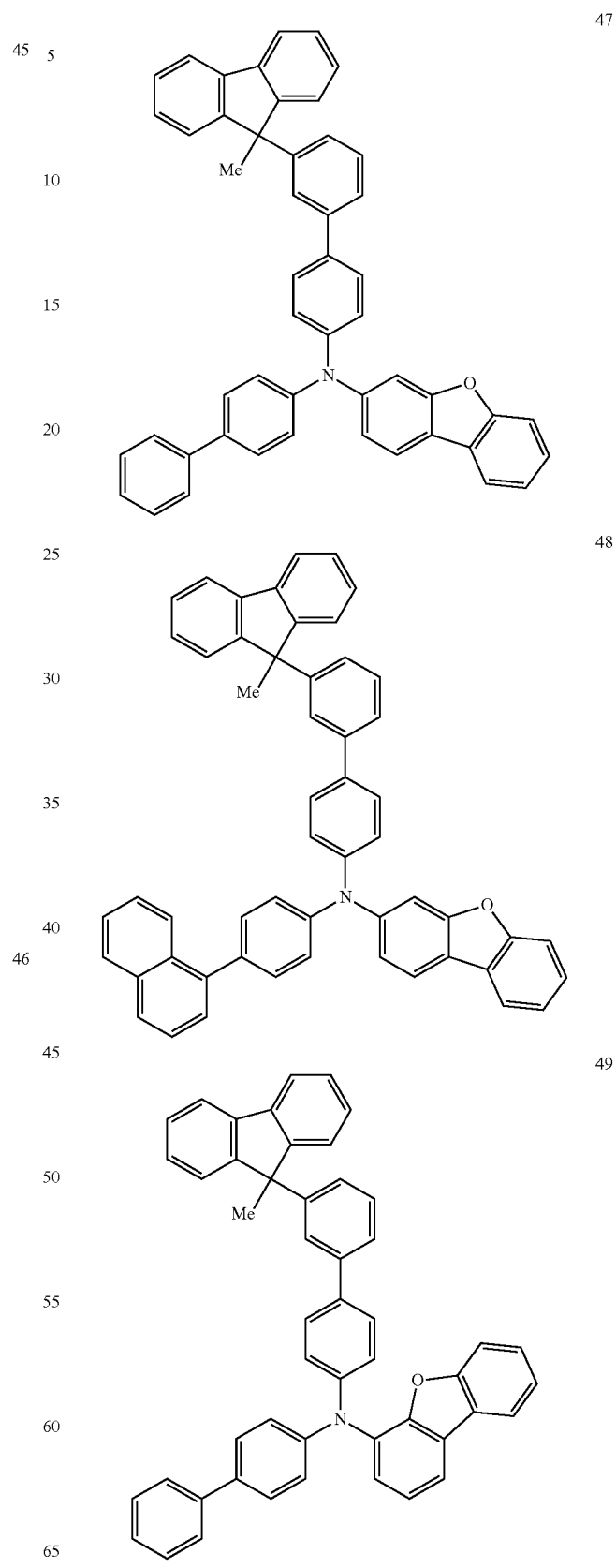

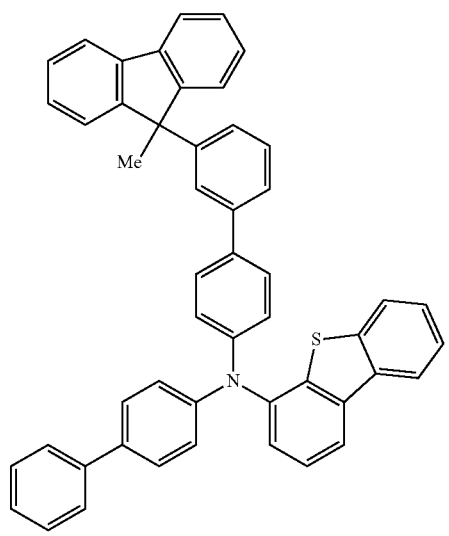
50
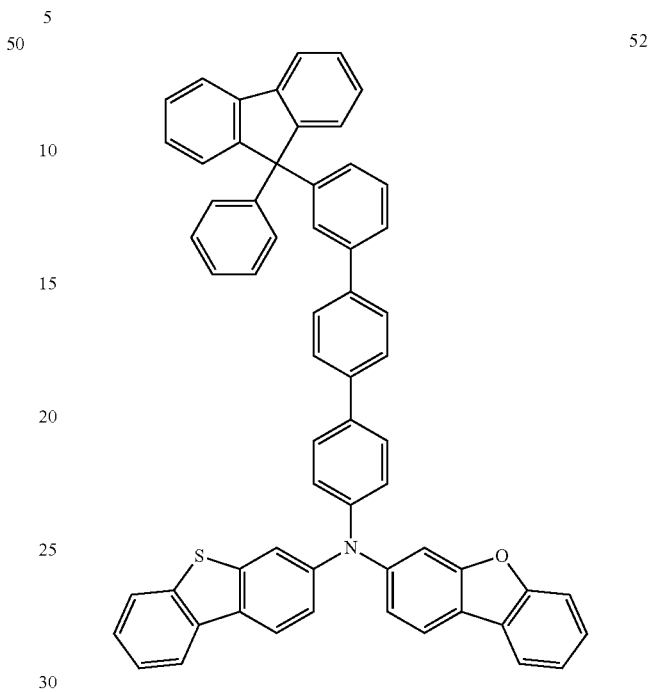
51
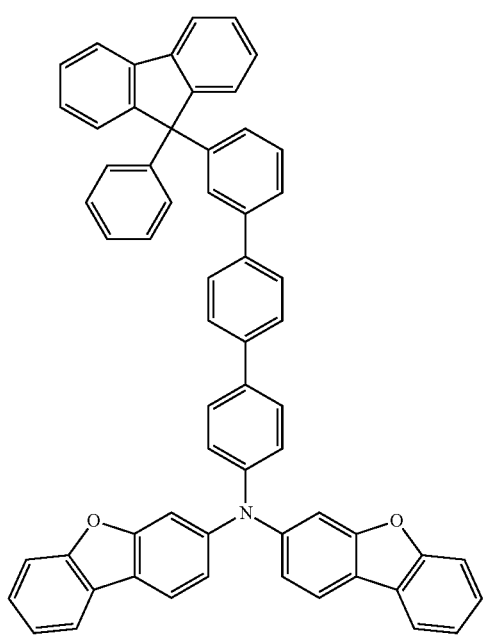
52
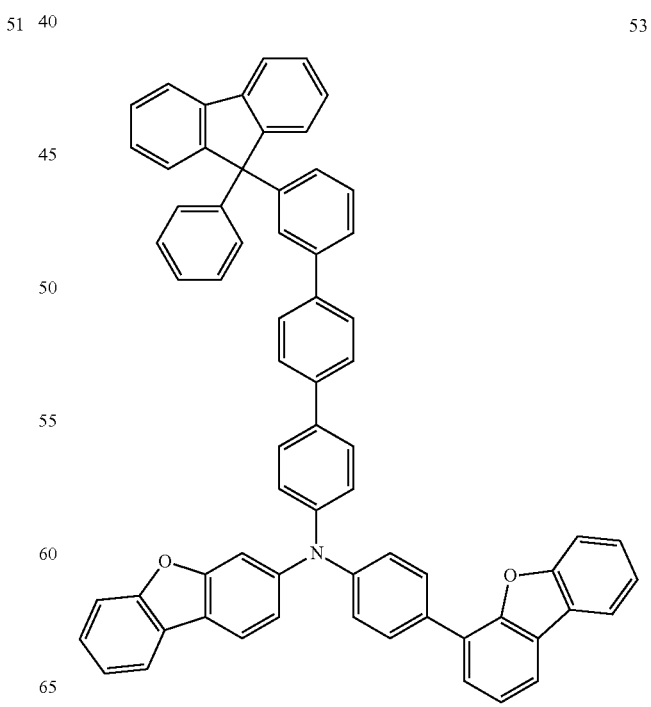
53

-continued

54

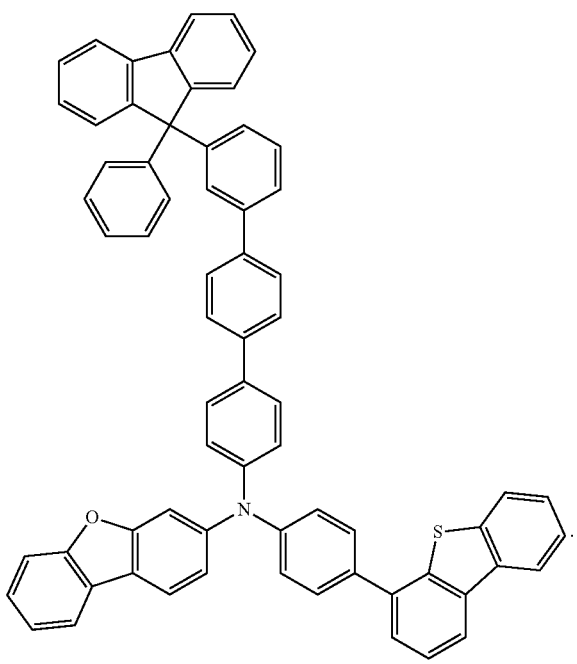

8. An organic electroluminescent device, comprising:
an anode,
a cathode,
an emission layer between the anode and the cathode, and
a plurality of lamination layers between the anode and the emission layer,
wherein at least one of the plurality of lamination layers comprises an amine compound represented by the following Formula 1:

Formula 1

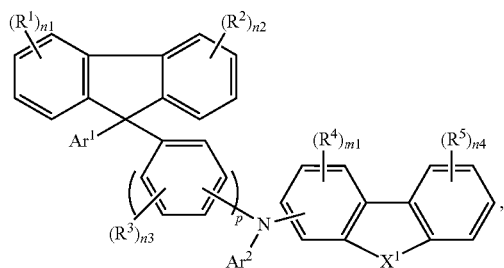

wherein, in the Formula 1,
$X^1$ is O or S;
$Ar^1$ and $Ar^2$ are each independently selected from a substituted or unsubstituted aryl group having 6 to 30 carbon atoms for forming a ring and a substituted or unsubstituted heteroaryl group having 2 to 30 carbon atoms for forming a ring;
$R^1$, $R^2$, $R^4$, and $R^5$ are each independently selected from a substituted or unsubstituted alkyl group having 1 to 10 carbon atoms, a substituted or unsubstituted cycloalkyl group having 5 to 10 carbon atoms for forming a ring, a substituted or unsubstituted aryl group having 6 to 20 carbon atoms for forming a ring, and a 5- to 7-membered ring structure obtained through bonding of any adjacent substituents;

$R^3$ is a substituted or unsubstituted alkyl group having 1 to 10 carbon atoms;
n1 to n4 are each independently an integer selected from 0 to 4;
m1 is an integer selected from 0 to 3; and
p is an integer selected from 1 to 3,
wherein in the amine compound represented by Formula 1, at least one of the p number of phenylene groups connecting a fluorenyl group and an arylamino group connects the flourenyl group and the arylamino group at a meta position.

9. The organic electroluminescent device of claim 8, wherein the amine compound is included in a layer between the anode and the emission layer and adjacent to the emission layer.

10. The organic electroluminescent device of claim 8, further comprising a hole injection layer and a hole transport layer between the anode and the emission layer, wherein the amine compound is included in at least one selected from the hole injection layer and the hole transport layer.

11. The organic electroluminescent device of claim 10, wherein:
the hole injection layer is on the anode;
the hole transport layer is on the hole injection layer; and
wherein the hole transport layer includes the amine compound.

12. The organic electroluminescent device of claim 8, wherein, in the amine compound represented by the above Formula 1, the $Ar^1$ is a substituted or unsubstituted aryl group or a substituted or unsubstituted heteroaryl group, each independently obtained through 2- or 3-ring condensation of any of 5- to 6-membered aromatic and heteroaromatic rings.

13. The organic electroluminescent device of claim 8, wherein, in the amine compound represented by the above Formula 1, the $Ar^2$ is a substituted or unsubstituted aryl group or a substituted or unsubstituted heteroaryl group, each independently obtained through 2- or 3-ring condensation of any of 5- to 6-membered aromatic and heteroaromatic rings.

14. The organic electroluminescent device of claim 13, wherein the $Ar^2$ is represented by the following Formula 2:

Formula 2

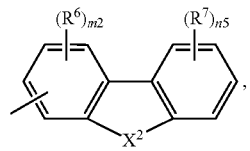

wherein, in the Formula 2,
$X^2$ is O or S;
$R^6$ and $R^7$ are each independently selected from a substituted or unsubstituted alkyl group having 1 to 10 carbon atoms, a substituted or unsubstituted cycloalkyl group having 5 to 10 carbon atoms for forming a ring, a substituted or unsubstituted aryl group having 6 to 20 carbon atoms for forming a ring, and a 5- to 7-membered ring structure obtained through bonding of any adjacent substituents;
n5 is an integer selected from 0 to 4; and
m2 is an integer selected from 0 to 3.

15. The organic electroluminescent device of claim 8, wherein the $Ar^1$ and $Ar^2$ are each independently selected from the group consisting of a fluorenyl group, an anthryl group, a naphthyl group, a dibenzofuranyl group, a dibenzothiophenyl group, a carbazolyl group, a phenanthrenyl group, an indolyl group, a quinolyl group, and combinations thereof.

16. The organic electroluminescent device of claim 8, wherein the amine compound represented by the above Formula 1 comprises at least one of Compounds 1 to 19 collectively denoted as Formula 3:

Formula 3

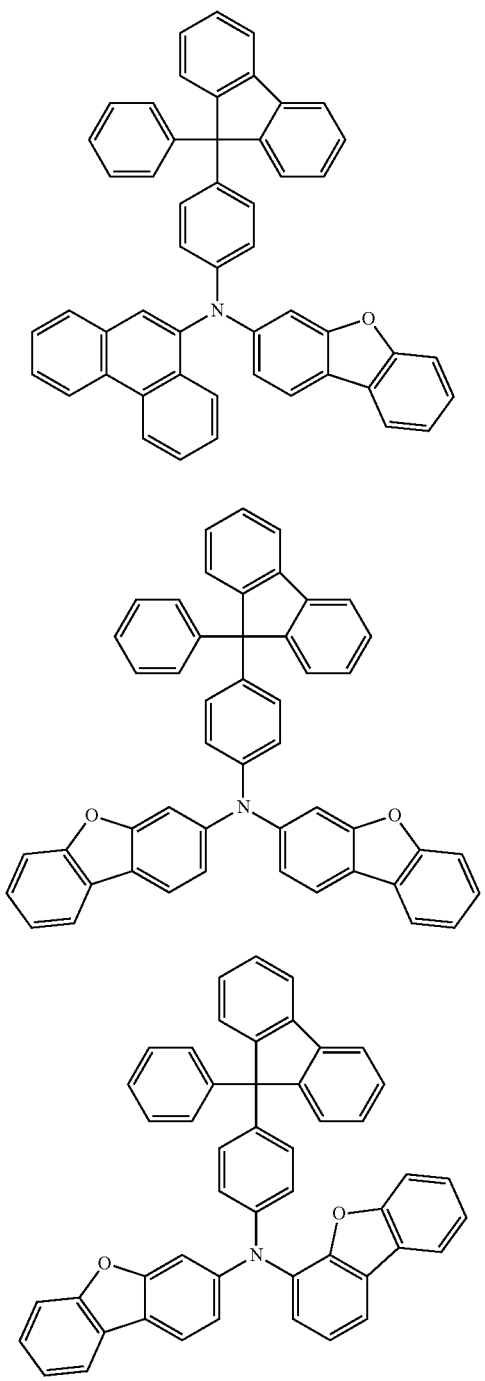

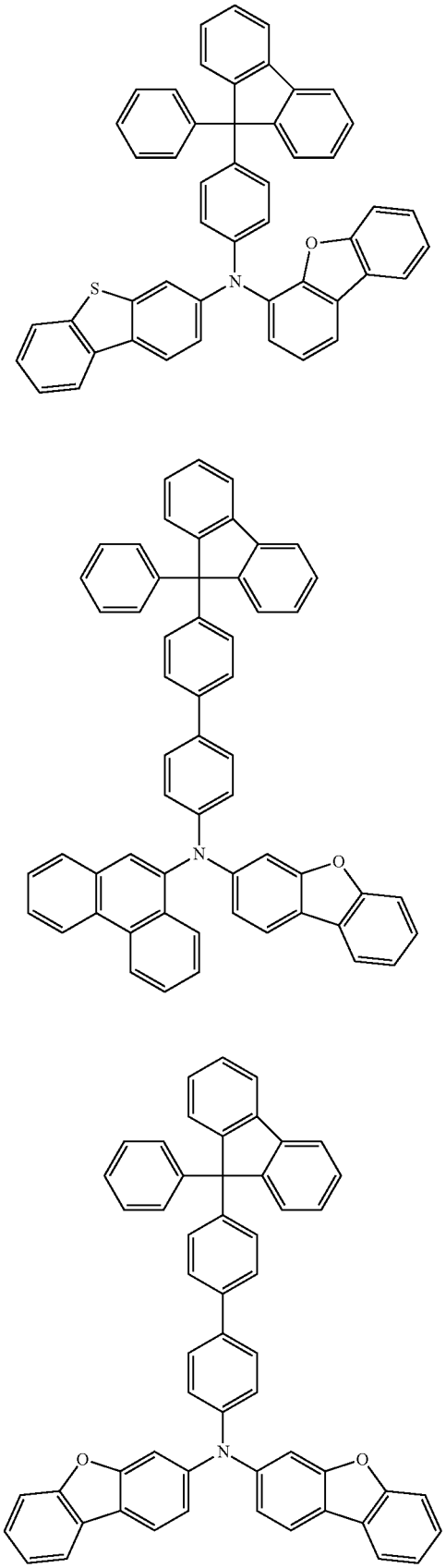

7
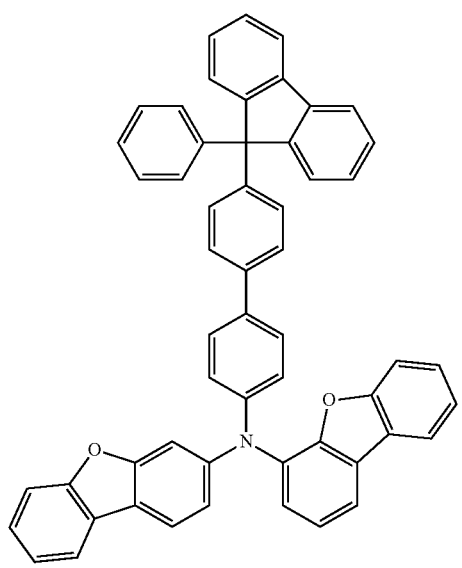
8
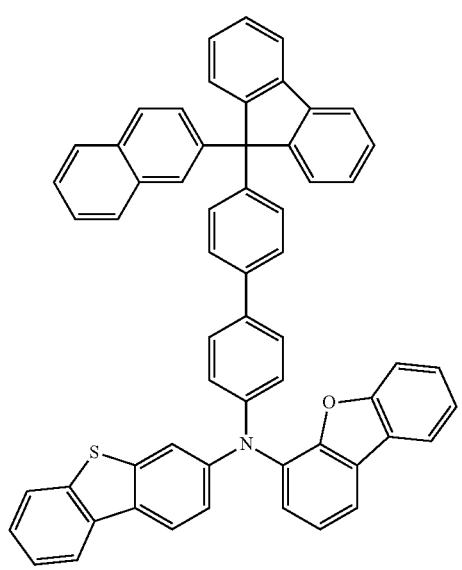
9
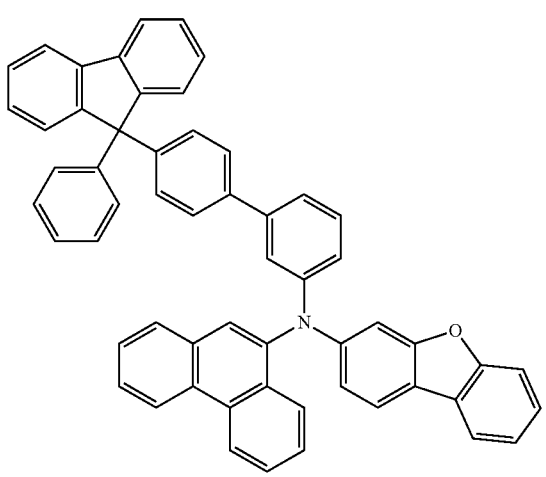
10
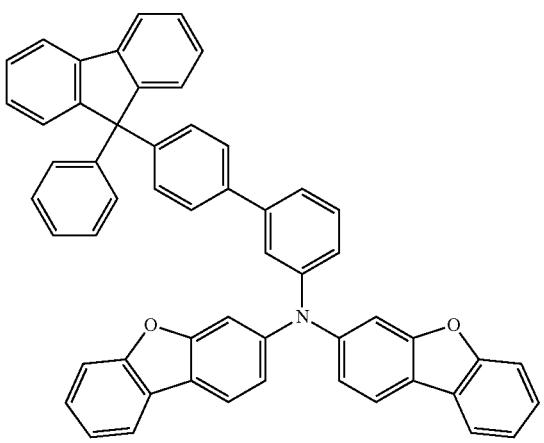
11
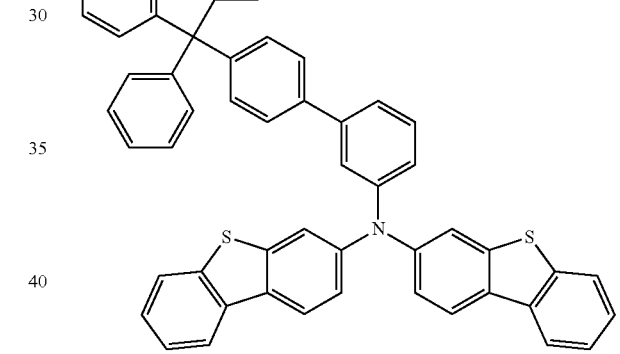
12
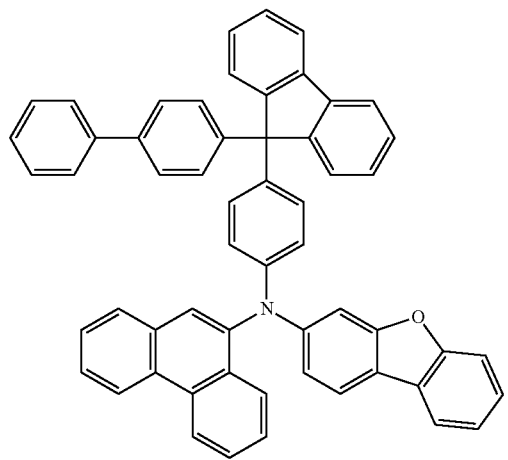

13
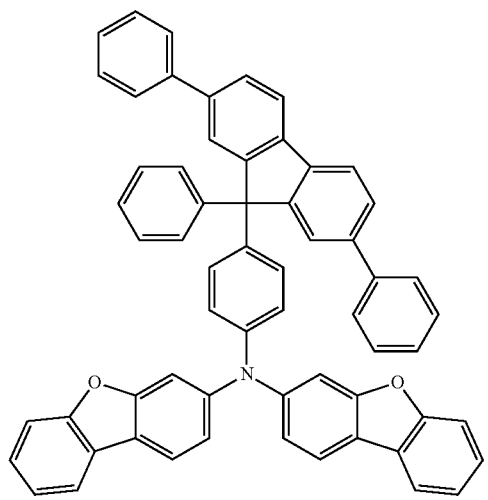
14
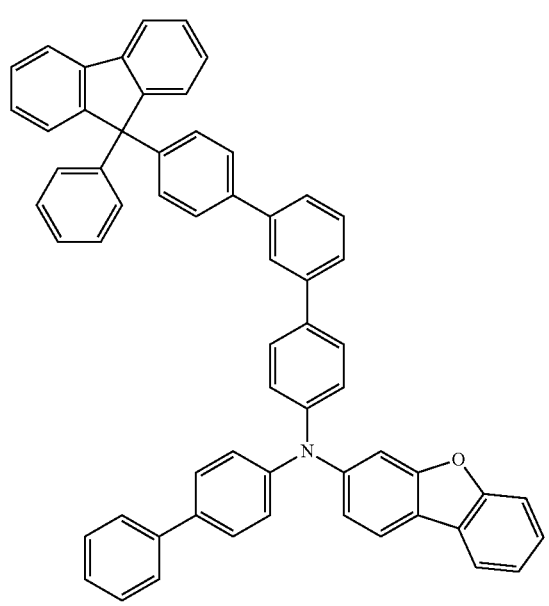
15
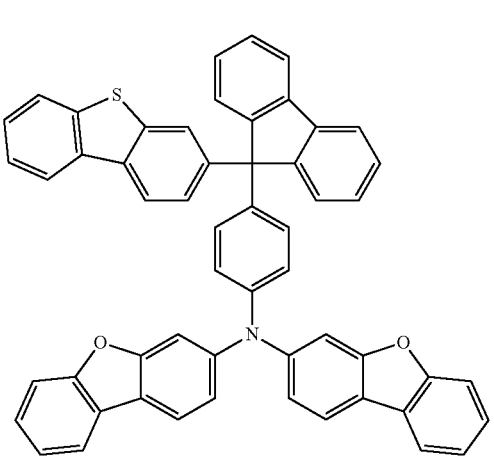
16
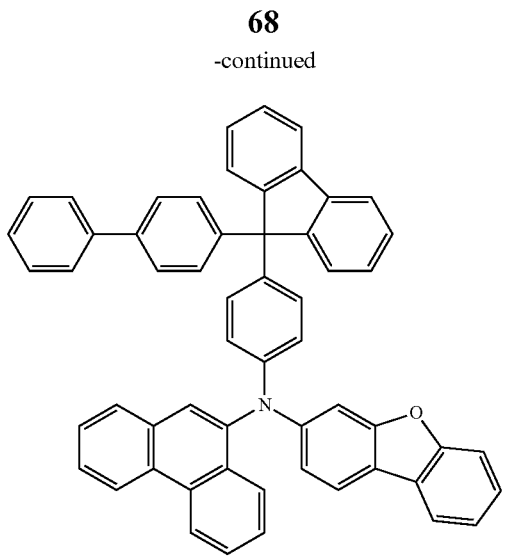
17
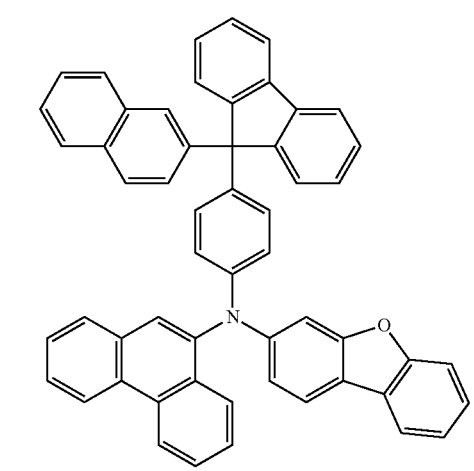
18
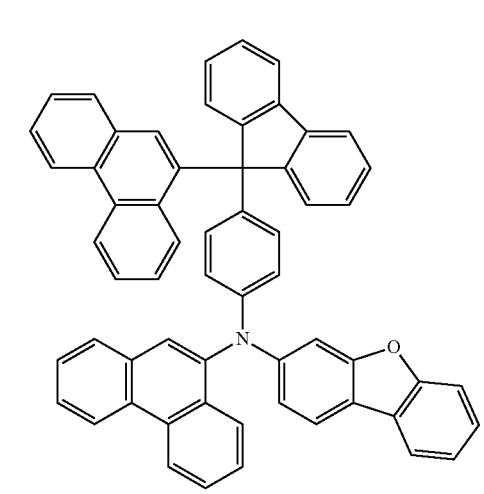

19
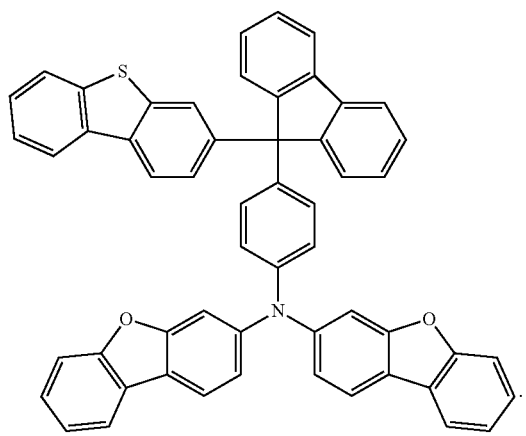
17. The organic electroluminescent device of claim 8, wherein the amine compound represented by the above Formula 1 comprises at least one of Compounds 20 to 42 collectively denoted as Formula 4:
Formula 4
20
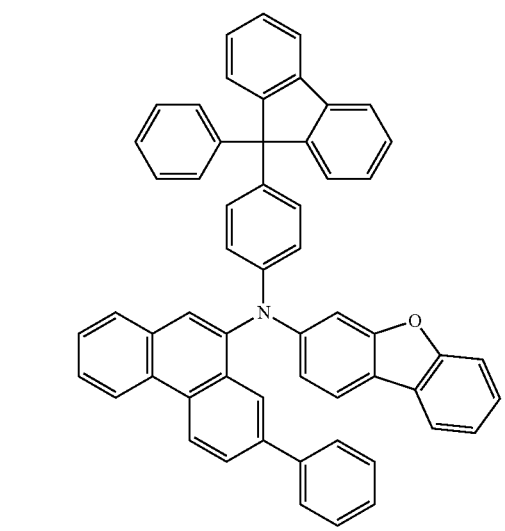
21
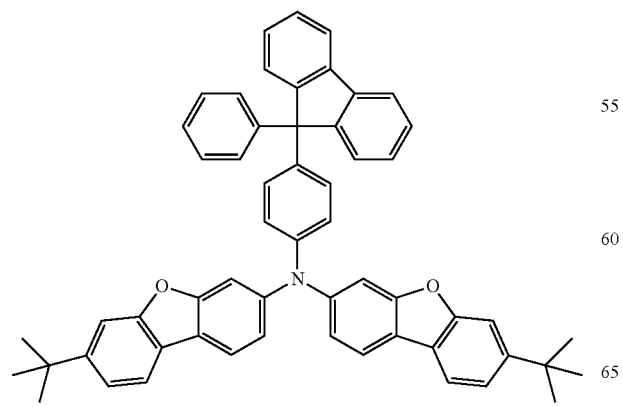
22
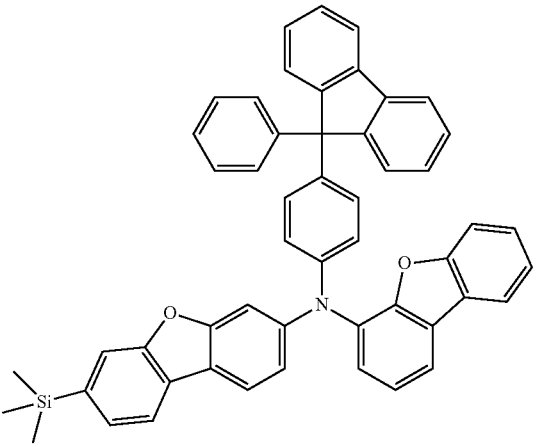
23
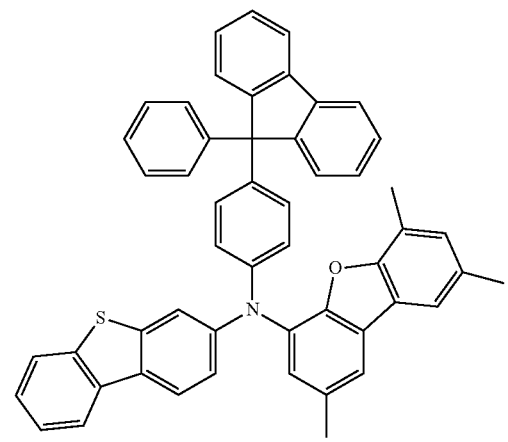
24
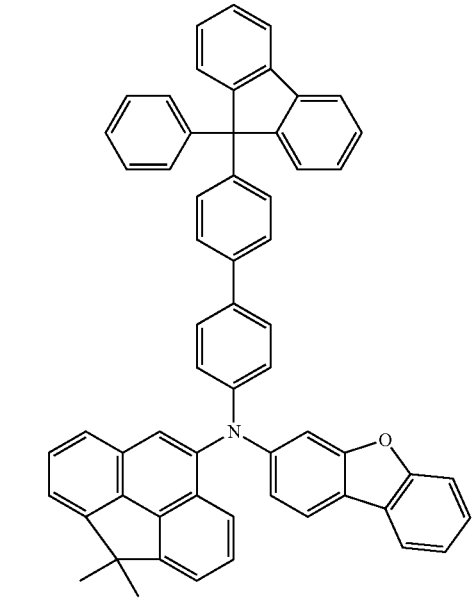

25
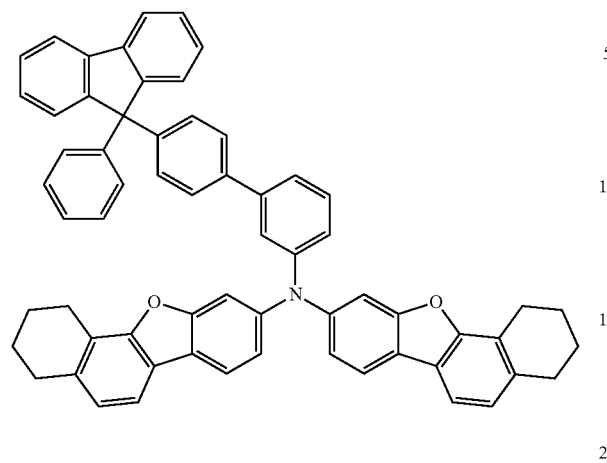
26
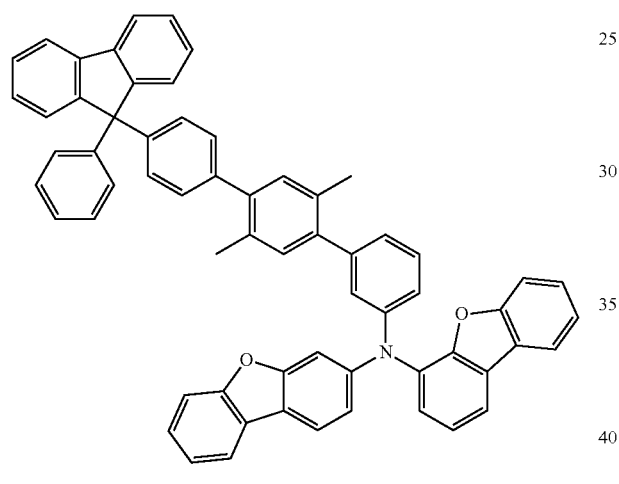
27
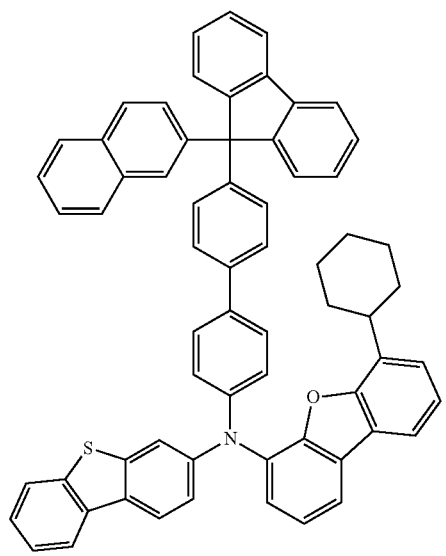
28
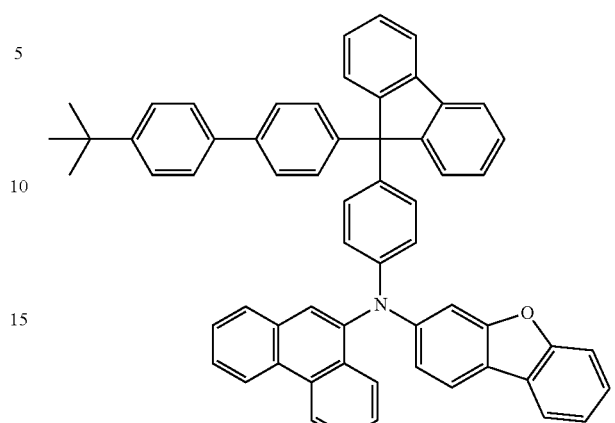
29
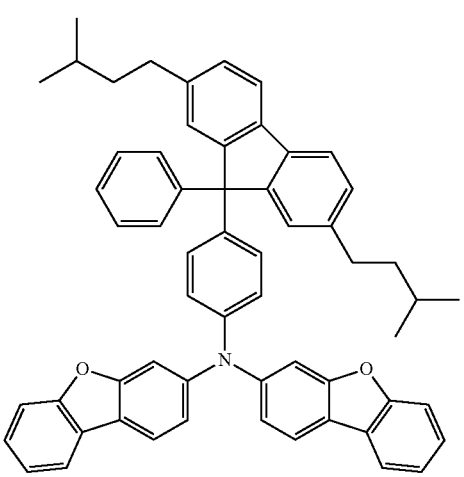
30
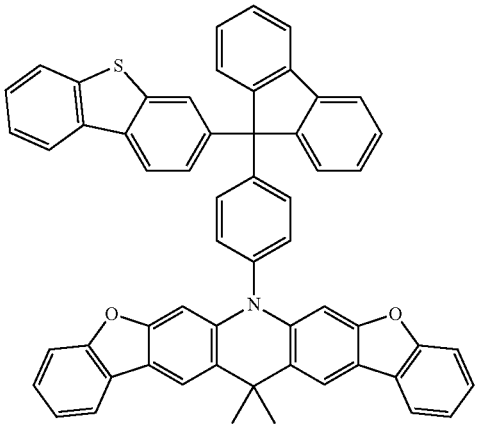

31
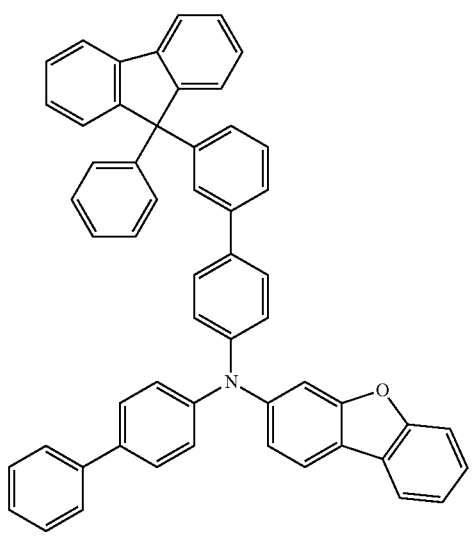
32
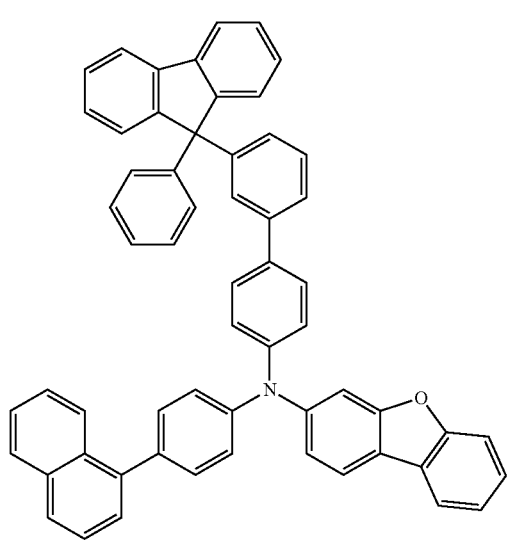
33
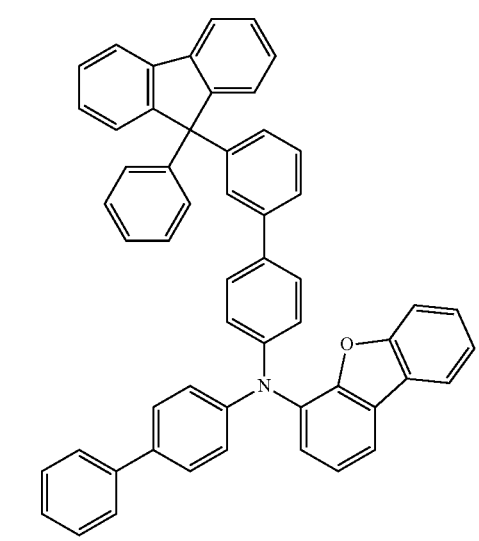
34
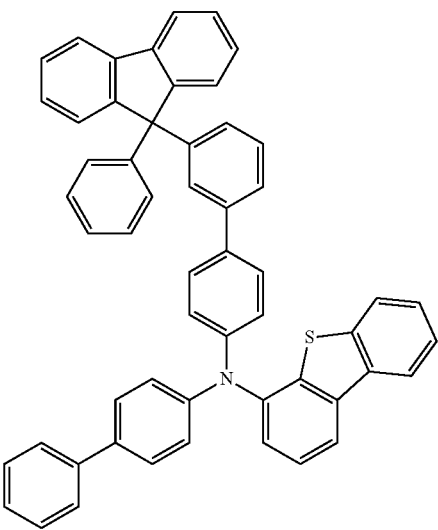
35
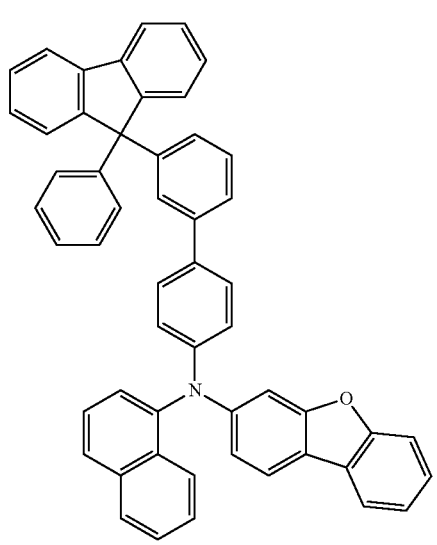
36
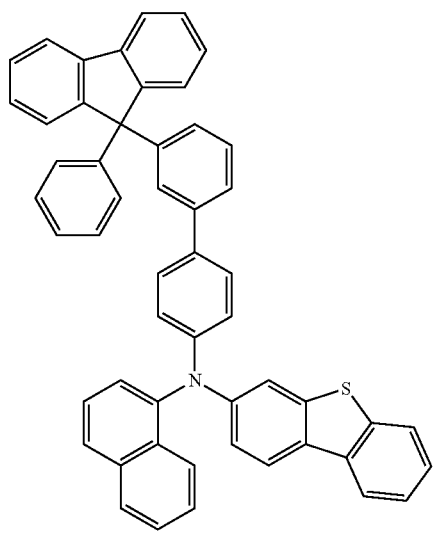

37
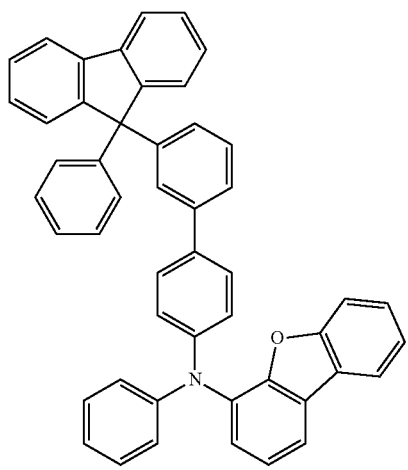
38
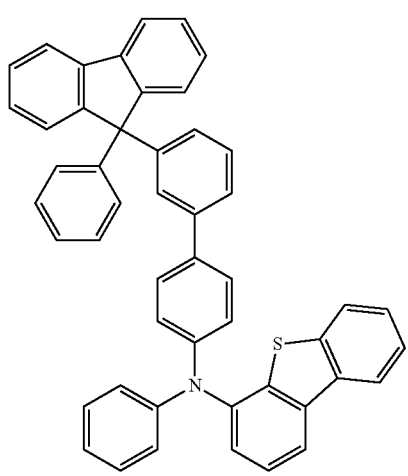
39
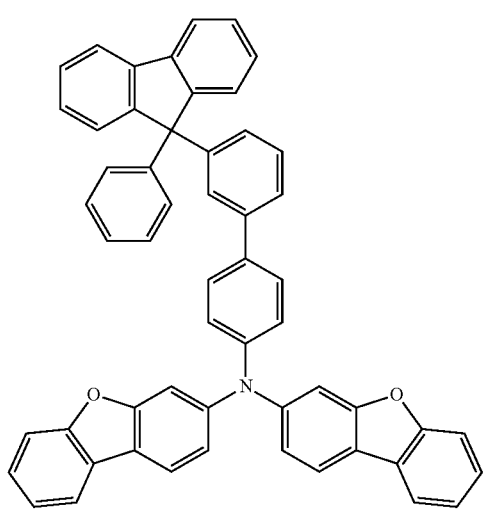
40
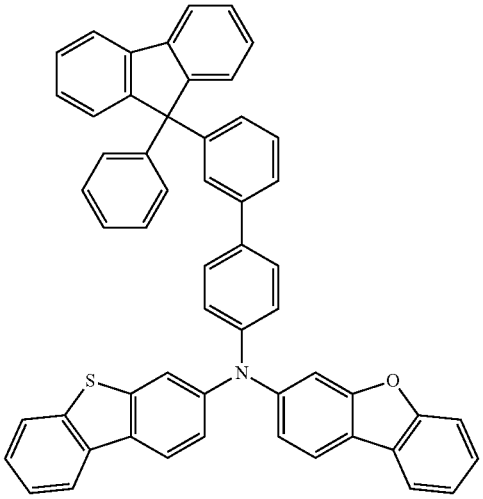
41
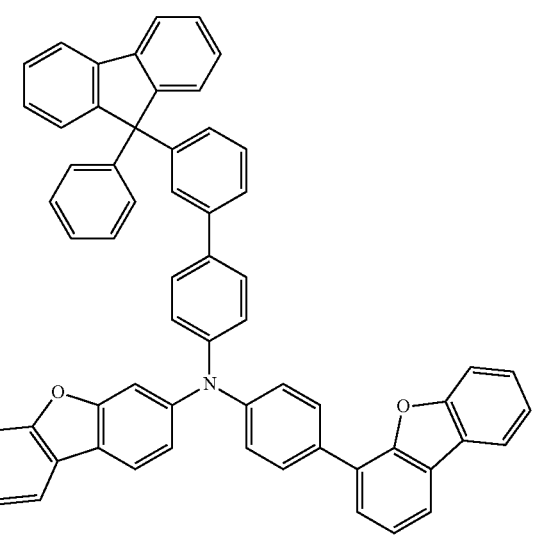
42
18. The organic electroluminescent device of claim 8, wherein the amine compound represented by the above Formula 1 comprises at least one of Compounds 43 to 54 collectively denoted as Formula 5:
Formula 5
43
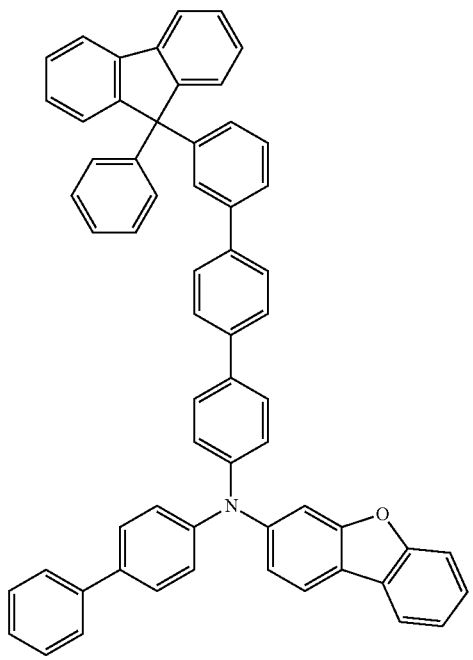
44
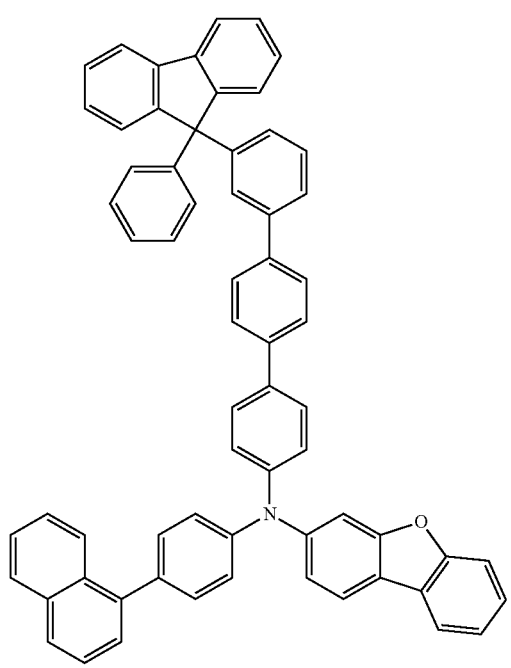
45
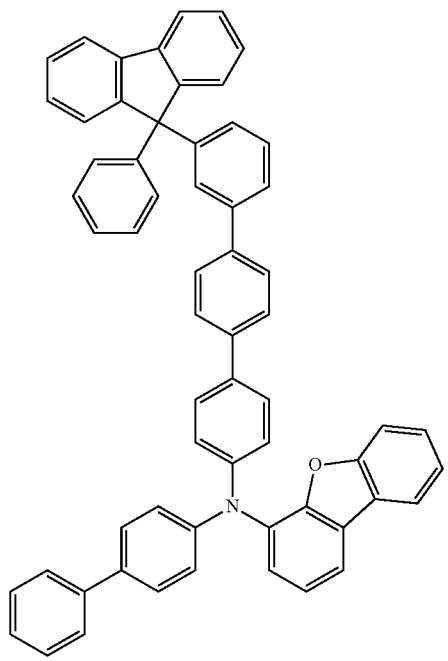
46

47
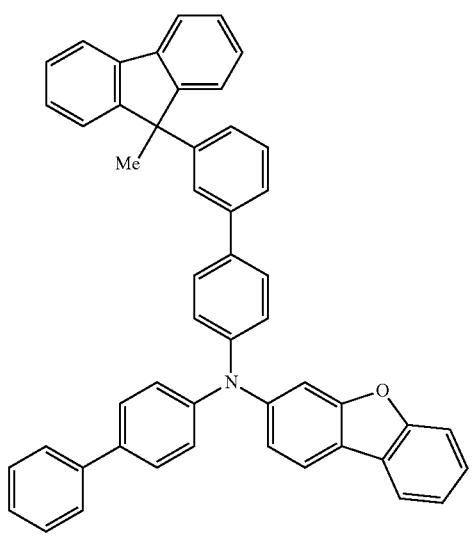
48
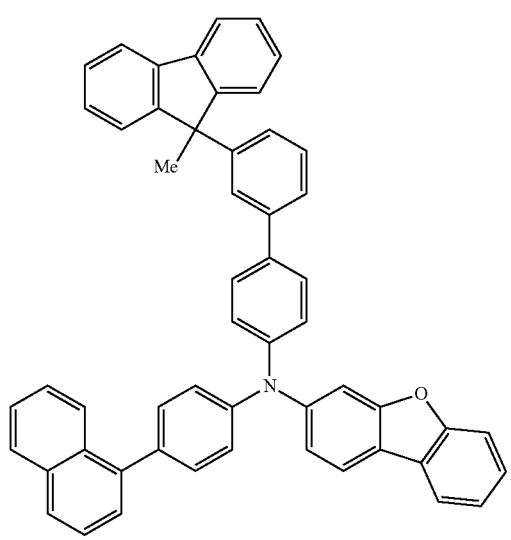
49
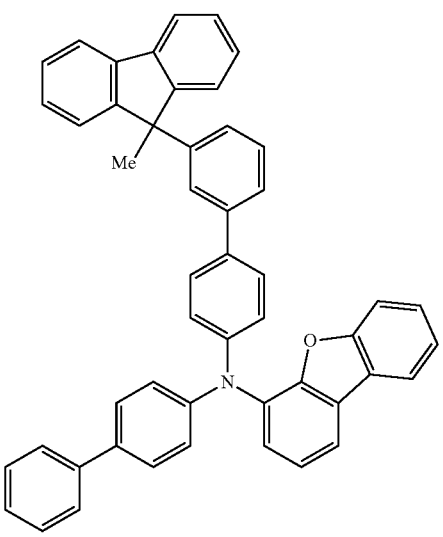
50
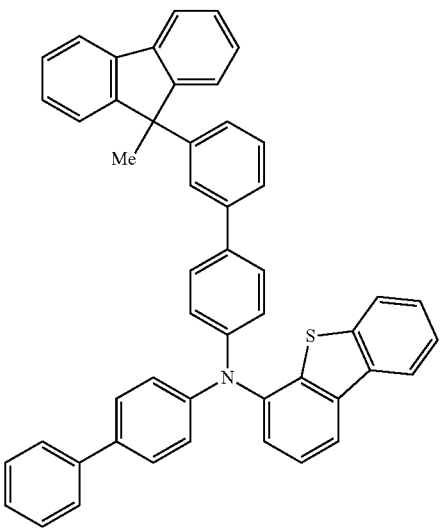

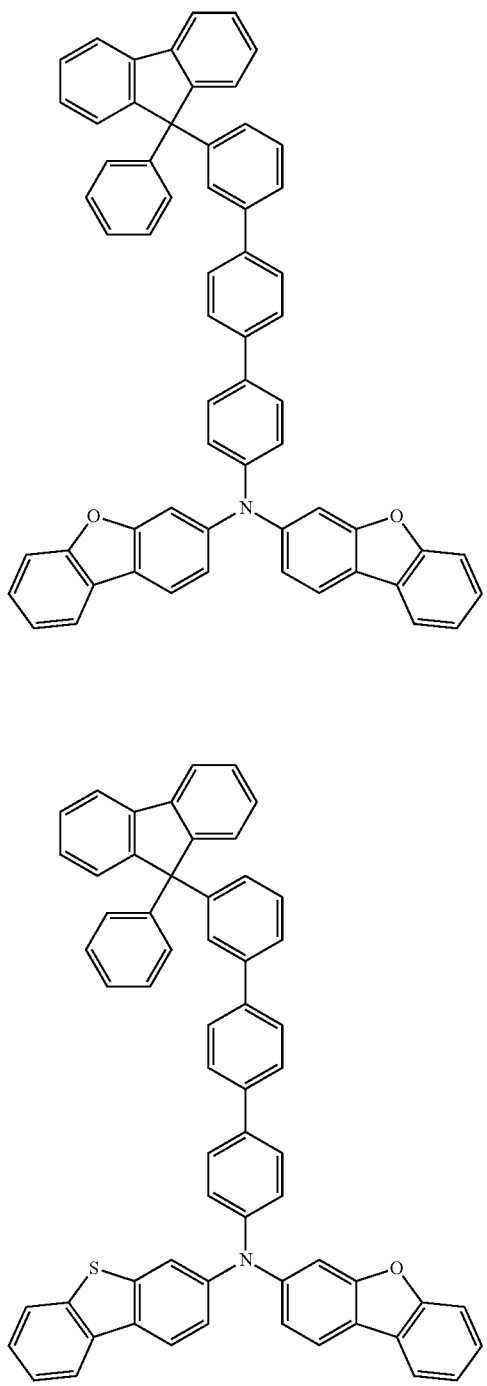
51
52
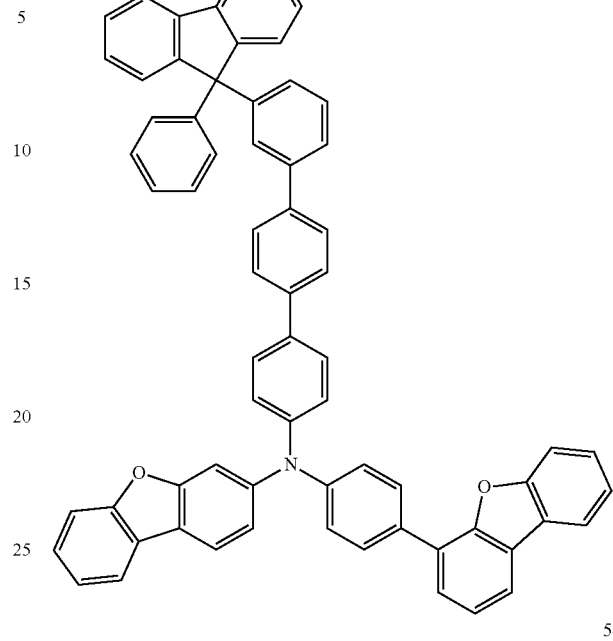
53
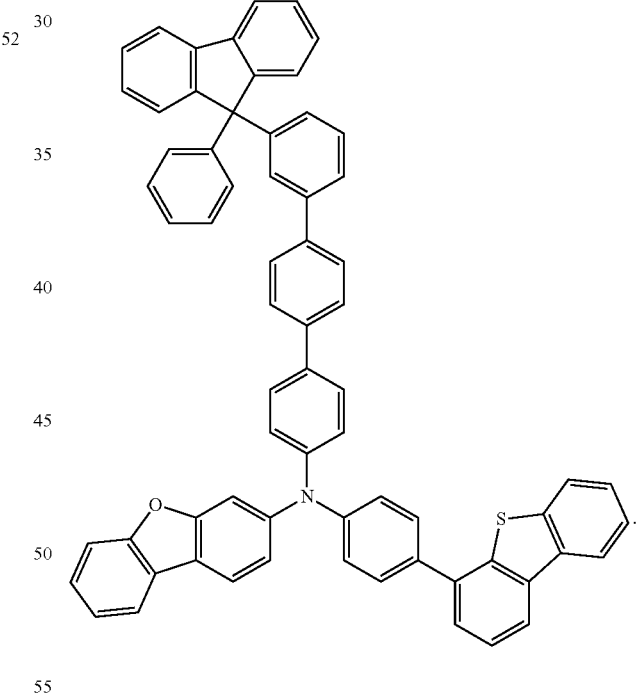
54
* * * * *